(12) United States Patent
Suyker et al.

(10) Patent No.: US 10,675,034 B2
(45) Date of Patent: Jun. 9, 2020

(54) ANASTOMOSIS DEVICE FOR MAKING ANASTOMOSES BETWEEN HOLLOW STRUCTURES

(71) Applicant: Innovative Interventional Technologies, B.V., Amsterdam (NL)

(72) Inventors: Paulus Thomas Wilhelmus Suyker, Amsterdam (NL); Wilhelmus Joseph Leonardus Suyker, Zwolle (NL)

(73) Assignee: Innovative Interventional Technologies, B.V. (NL)

( * ) Notice: Subject to any disclaimer, the term of this patent is extended or adjusted under 35 U.S.C. 154(b) by 224 days.

(21) Appl. No.: 15/566,100

(22) PCT Filed: Mar. 22, 2016

(86) PCT No.: PCT/EP2016/056297
§ 371 (c)(1),
(2) Date: Oct. 12, 2017

(87) PCT Pub. No.: WO2016/165918
PCT Pub. Date: Oct. 20, 2016

(65) Prior Publication Data
US 2018/0110524 A1    Apr. 26, 2018

Related U.S. Application Data

(60) Provisional application No. 62/146,485, filed on Apr. 13, 2015.

(51) Int. Cl.
*A61B 17/11* (2006.01)
*A61B 17/064* (2006.01)
(Continued)

(52) U.S. Cl.
CPC ........ *A61B 17/11* (2013.01); *A61B 17/00234* (2013.01); *A61B 17/0644* (2013.01);
(Continued)

(58) Field of Classification Search
CPC .......... A61B 17/00234; A61B 17/0644; A61B 17/11; A61B 17/1152; A61B 17/1155;
(Continued)

(56) References Cited

U.S. PATENT DOCUMENTS

| 4,350,160 A | 9/1982 | Kolesov et al. |
| 4,366,819 A | 1/1983 | Kaster et al. |

(Continued)

FOREIGN PATENT DOCUMENTS

| WO | WO0056228 A1 | 9/2000 |
| WO | 0238055 A2 | 5/2002 |
| WO | 2005086841 A2 | 9/2005 |

OTHER PUBLICATIONS

Suyker, Willem JL, et al. "S 2 Connector Versus Suture." Circulation 114.1 suppl (2006): I-390.
(Continued)

*Primary Examiner* — Kathleen S Holwerda
*Assistant Examiner* — Brooke Labranche
(74) *Attorney, Agent, or Firm* — Mendelsohn Dunleavy, P.C.

(57) ABSTRACT

The present invention relates to an anastomosis system for realizing anastomosis between first and second hollow structures, such as end-to-side anastomosis, by way of a joining member and an applicator. The anastomosis system comprises an annular joining member adapted for joining the first and second hollow structures, a tubular member adapted to position the joining member at or proximate to a distal end of the second hollow structure and to be at least partially inserted into the second hollow structure, a support member adapted to hold the second hollow structure and a mechanism, for actuating the joining member when positioned at or proximate to the distal end of the second hollow structure,
(Continued)

which joining member is actuated substantially radially relative to a longitudinal axis of the tubular member.

17 Claims, 13 Drawing Sheets

(51) Int. Cl.
| | | |
|---|---|---|
| *A61B 17/115* | (2006.01) | |
| *A61B 17/322* | (2006.01) | |
| *A61B 17/00* | (2006.01) | |
| *A61F 2/06* | (2013.01) | |
| *A61B 90/00* | (2016.01) | |

(52) U.S. Cl.
CPC ........ *A61B 17/1152* (2013.01); *A61B 17/322* (2013.01); *A61B 17/1155* (2013.01); *A61B 2017/00243* (2013.01); *A61B 2017/00252* (2013.01); *A61B 2017/00455* (2013.01); *A61B 2017/00526* (2013.01); *A61B 2017/00969* (2013.01); *A61B 2017/0641* (2013.01); *A61B 2017/1107* (2013.01); *A61B 2017/1135* (2013.01); *A61B 2017/1157* (2013.01); *A61B 2017/3225* (2013.01); *A61B 2090/0807* (2016.02); *A61B 2090/3937* (2016.02); *A61F 2/064* (2013.01)

(58) Field of Classification Search
CPC ........ A61B 17/322; A61B 2017/00243; A61B 2017/00455; A61B 2017/00526; A61B 2017/0641; A61B 2017/1107; A61B 2017/1135; A61B 2017/1157; A61B 2017/3225; A61B 2017/00252; A61B 2017/00969; A61B 2090/0807; A61B 2090/3937; A61F 2/064

See application file for complete search history.

(56) References Cited

U.S. PATENT DOCUMENTS

| | | | |
|---|---|---|---|
| 4,368,736 A | 1/1983 | Kaster et al. | |
| 4,624,257 A | 11/1986 | Berggren et al. | |
| 4,917,090 A | 4/1990 | Berggren et al. | |
| 4,917,091 A | 4/1990 | Berggren et al. | |
| 5,234,447 A | 8/1993 | Kaster et al. | |
| 5,695,504 A | 12/1997 | Gifford, III et al. | |
| 5,707,380 A | 1/1998 | Hinchliffe et al. | |
| 5,833,698 A * | 11/1998 | Hinchliffe | A61B 17/1152 606/153 |
| 5,931,842 A | 8/1999 | Goldsteen et al. | |
| 5,976,178 A | 11/1999 | Goldsteen et al. | |
| 6,066,148 A | 5/2000 | Rygaard | |
| 6,074,416 A | 6/2000 | Berg et al. | |
| 6,485,496 B1 | 11/2002 | Suyker et al. | |
| 6,966,917 B1 | 11/2005 | Suyker et al. | |
| 7,018,387 B2 | 3/2006 | Suyker et al. | |
| 7,022,127 B2 | 4/2006 | Suyker et al. | |
| 7,063,711 B1 | 6/2006 | Loshakove et al. | |
| 7,666,198 B2 | 2/2010 | Suyker et al. | |
| 8,066,723 B2 | 11/2011 | Suyker et al. | |
| 8,182,498 B2 | 5/2012 | Suyker et al. | |
| 8,858,579 B2 | 10/2014 | Suyker et al. | |
| 9,675,357 B2 | 6/2017 | Suyker et al. | |
| 2003/0195535 A1 | 10/2003 | Swanson et al. | |
| 2004/0176786 A1 | 9/2004 | Edoga et al. | |
| 2005/0203551 A1 | 9/2005 | Weadock et al. | |
| 2005/0288693 A1 | 12/2005 | Suyker et al. | |
| 2006/0095055 A1 | 5/2006 | Douglas et al. | |
| 2006/0095056 A1 | 5/2006 | Douglas et al. | |
| 2009/0112304 A1 | 4/2009 | Weadock et al. | |
| 2013/0186935 A1* | 7/2013 | Edoga | A61B 17/072 227/178.1 |
| 2013/0296890 A1* | 11/2013 | Sgarzani | A61B 17/11 606/142 |

OTHER PUBLICATIONS

Suyker, Willem JL, et al. "Stapled coronary anastomosis with minimal intraluminal artifact: The S 2 Anastomotic System in the off-pump porcine model." The Journal of thoracic and cardiovascular surgery 127.2 (2004): 498-503.

Budde, Ricardo PJ, et al. "Quality assessment of distal S2AS connector anastomosis by 13 MHz epicardial ultrasound." European journal of cardio-thoracic surgery 28.6 (2005): 833-837.

International Search Report and Written Opinion; dated Sep. 20, 2016 for PCT Application No. PCT/EP2016/056297.

Suyker, Willem JL. "Micro-Connector Constructed Coronary Anastomosis." (2008), Chapter 8, pp. 113-120.

Suyker, Willem JL, and Cornelius Borst. "Coronary connector devices: analysis of 1,469 anastomoses in 1,216 patients." The Annals of thoracic surgery 85.5 (2008): 1828-1836.

Communication pursuant to Article 94(3) EPC for corresponding European Application No. 16720353.8; dated Oct. 28, 2019 (5 pages).

* cited by examiner

ANASTOMOSIS DEVICE FOR MAKING ANASTOMOSES BETWEEN HOLLOW STRUCTURES

BACKGROUND OF THE INVENTION

1. Field of the Invention

The present invention relates generally to the field of anastomosis devices and methods. More particularly, the present invention relates to a vascular anastomosis apparatus and methods for using such apparatus for vascular anastomoses between hollow structures.

2. Description of the Related Technology

An anastomosis is the surgical joining of hollow structures, such as blood vessels having a lumen, to create fluid communication between the lumens of the joined structures. Depending on the diameters of the structures to be joined, anastomoses can have a wide range of sizes, and can have any of the following geometries: end-to-side, side-to-side and end-to-end. Anastomoses are employed in, for example, vascular surgery for the purpose of restoring the blood flow in obstructed arteries or for the purpose of connecting transplanted organs or implantable devices. One example of this is the implantation of artificial hearts, a procedure designed to restore normal blood flow by connecting a blood pump in order to assist or replace a failing heart.

Anastomoses can also be employed in, for example, cardiac surgery for the purpose of providing access to a vital structure like the heart. One example of this is the connection of a vascular prosthesis to the right or left atrium of the heart for the purpose of inserting into the heart an intracardiac repair device, such as an atrial septal closure device, a mitral valve repair or replacement device. This may preferably be carried out by placing the device at the desired location and deploying the device without the need to surgically open the heart in order to avoid the need for a cardiopulmonary bypass with a heart lung machine.

Vascular anastomoses can be created by hand suturing. This is a time-consuming and difficult task requiring a high degree of surgical skill due to the considerable perfection required to achieve reliable and consistent functionality of the sutured structures. Consequently, hand suturing poses a relatively high risk to the patient, because the overall outcome is entirely dependent on the functionality of the sutured structures. Not only does the surgeon have to provide a leak-free connection of vessel walls, but also the anastomosis must provide a smooth, open path for blood flow. Further, the structures involved are quite small and thus the required degree of precision is such that optical magnification is often needed for carrying out the suturing process. In this method, there is frequently a need for additional suturing of the anastomosis to close leaks that may be detected after the initial suturing has been completed. Besides the required precision, the time-consuming nature of creating a hand-sutured anastomosis is of special concern. Also, the surgical field must be sufficient to provide ample access to carry out the required suturing movements using suitable instruments. This will require a relatively large incision in the patient that may substantially increase patient trauma for this procedure. Particularly in feeble patients, such as those with a failing heart that require an implantable assist device, reducing procedural trauma by providing procedures that can be carried out using small incisions is highly desirable and will improve the outcome.

In order to reduce the difficulty of producing a vascular anastomosis and facilitate limited access procedures, it is desirable to provide a precise and expedient way for making a reliable anastomosis between a vessel graft, either prosthetic or natural, and the native blood vessel.

One approach involves the use of stapling technology. However, instruments for stapling are not easily adaptable for creating a vascular anastomosis. This is because of the more demanding requirements for vascular connections due to the need for such connections to be watertight and have a smooth, unobstructed inner geometry so as to avoid creation of a flow pressure gradient in the vessel. Also, the vascular walls need to be handled delicately to avoid tissue trauma that may cause thrombosis or chronic tissue proliferation, both potentially leading to partial or even complete vessel lumen obstruction. Various attempts have been made to provide such vascular stapling devices, such as in U.S. Pat. Nos. 4,350,160 and 5,234,447. Other approaches to this problem are found in, for example, in U.S. Pat. Nos. 4,366,819; 4,368,736; 4,624,257; 4,917,090; 4,917,091; 5,695,504; 6,074,416; 5,931,842; 5,976,178; 6,066,148; 5,833,698 and 5,707,380.

Elements of anastomosis systems are known from, for example, U.S. Pat. Nos. 6,485,496; 6,966,917; 7,018,387; 7,022,127; 7,666,198; 8,066,723; 8,182,498 and US 2009/0112304 A1. These publications relate to anastomosis devices that include a joining member and an applicator. One embodiment of these devices comprises an annular or tubular joining member that is adapted to be endoluminally expanded and permanently deformed to create an anastomosis between two structures whereby fluid can flow from one structure into and through a lumen in the other structure. These devices also include an applicator designed to provide a specific sequence of movements to cause expansion and deformation of the joining member and thereby create the anastomosis. The applicator typically includes a tubular member including an expander, an outer tube that is expandable, an expandable inner tube that provides a seat for the joining member, and a mechanism for causing the specific sequence of movements for expansion and deformation of the joining member. The inner and outer tubes are typically rendered expandable by the provision of longitudinal slits along the length of each tube.

The practical advantages of providing side-to-side anastomoses (as in the system discussed above), over hand-suturing have been described in several published scientific papers: "$S^2$ *Connector versus suture: distal coronary anastomosis remodeling, patency and function in the pig*", Circulation. 2006; 114:1390-5; "*Stapled coronary anastomosis with minimal intraluminal artifact*: The $S^2$ Anastomotic System in the off-pump porcine model." J Thorac Cardiovasc Surg. 2004; 127:498-503; "*Quality assessment of distal $S^2AS$ connector anastomosis by* 13 *MHz epicardial ultrasound*." Eur J Cardiothorac Surg. 2005; 28: 833-7.

Depending on the anastomosis geometry this prior art may, however, have limitations. For example, in the case of an end-to-side anastomosis wherein the longitudinal axes of the hollow structures are at an angle smaller than 90°, the joining member may fail to properly engage part of the wall of the bevelled end of the second hollow structure. This phenomenon is believed to be caused by a reduced radial stability of the most distal end of the bevel of the second hollow structure, referred to as "the toe", during creation of the anastomosis. As a result, the anastomosis may immediately leak or may be weakened and may disintegrate upon movement of or exertion of force on the hollow structures.

The vast majority of vascular anastomotic and cardiac procedures are still performed by hand-suturing, thereby requiring full-length surgical incisions. Therefore there remains a need for easy to use anastomosis devices that can be used to easily perform a reliable vascular anastomosis and have a suitable size and geometry for use with a small incision.

SUMMARY OF THE INVENTION

An aspect of the present invention is an anastomosis device for creating an anastomosis between first and second hollow structures including a joining member and an applicator. The joining member is adapted for joining the first and second hollow structures. The applicator includes a tubular member adapted to position the joining member proximate to a distal end of the second hollow structure and at least partially within the second hollow structure, a support member adapted to support the second hollow structure and a mechanism for actuating the joining member when positioned for joining the hollow structures. The actuator is also adapted to actuate the joining member for radial expansion relative to a longitudinal axis of the tubular member of the actuator to position the joining member for joining the hollow structures.

Another aspect of the present invention may be an expandable annular joining member usable in anastomosis procedures which is provided with a plurality of loops of deformable material which enable radial expansion of the joining member.

Still another aspect of the present invention may be a method of creating an anastomosis between first and second hollow structures optionally employing a device in accordance with the present invention.

Still yet another aspect of the present invention may be an annular or tubular graft material having a particular shape adapted for positioning on an anastomosis device and/or reliable attachment to a hollow structure to provide a fluid flow channel from said hollow structure through said graft material.

Yet another aspect of the invention may be a cutting device for cutting graft material to provide cut graft material having at least one end configured for creating a reliable anastomosis with a hollow structure to provide a fluid flow channel from said hollow structure through said graft material.

Still yet another embodiment may be a method of cutting graft material to provide cut graft material having at least one end configured for creating a reliable anastomosis with a hollow structure to provide a fluid flow channel from said hollow structure through said graft material.

Another aspect of the present invention may be an anastomosis kit for quickly and reliably creating an anastomosis between hollow structures, and, in particular, creating an end-to-side vascular anastomosis using a bevelled graft vessel. The anastomosis kit may include a joining member, an applicator, optionally a graft material, and one or more auxiliary devices. The joining member is an annular device adapted to be radially expanded and permanently deformed to create and maintain the anastomosis. The applicator provides a particular sequence of movements to cause expansion and deformation of the joining member. The applicator may include a support for holding, positioning and/or supporting the graft vessel during device actuation. The anastomosis kit is useful for providing a vascular anastomosis between a prosthetic vascular graft and, for example, the aorta for connecting implantable artificial hearts, but may also be used for other types of procedures such as connecting a tubular graft to a structure, such as the heart, in order to acquire access to the inside of the structure in a minimally invasive way.

Another aspect of the invention may be an anastomosis method for quickly and reliably creating an anastomosis optionally including a method for quickly and reliably cutting a bevelled vessel graft.

Another aspect of the present invention may be an anastomosis device for creating an anastomosis between first and second hollow structures including a tubular member having a seat for a joining member, the tubular member is configured to position the joining member with its joining elements proximate to a distal end of the second hollow structure and at least partially within the second hollow structure, an actuator for actuating the joining member when the joining elements are positioned proximate to the distal end of the second hollow structure in a substantially radial direction relative to a longitudinal axis of the tubular member, and a support member for providing radial support to the second hollow structure proximate to the distal end thereof during actuation of the joining member.

Still yet another aspect of the present invention may be a method of creating an anastomosis between first and second hollow structures, such as an end-to-side anastomosis, by means of a joining member including a plurality of joining means. The method may include at least steps of inserting a tubular member in the second hollow structure, the tubular member having a seat for the joining member, positioning the joining member with its plurality of joining elements located proximate to a distal end of the second hollow structure, actuating the joining member at least substantially radially relative to a longitudinal axis of the tubular member, and providing radial support to the second hollow structure at least proximate to the distal end thereof during actuation of the joining member.

Yet another aspect of the present invention may be a cutting device for cutting graft material to provide cut graft material suitable for creating an anastomosis with a hollow structure. The cutting device may include a housing with at least one opening for inserting the graft material into the housing and/or positioning the graft material for cutting, a support located inside the housing and configured for supporting the graft material during cutting thereof, a cutting element operatively associated with said support for cutting the graft material when the graft material is positioned on the support. The cutting element is adapted to cut off at least a portion of one end of the graft material to provide a cut graft material having a predetermined shape suitable for creating an anastomosis.

Another aspect of the present invention may be an annular or tubular graft material, wherein an edge of at least one end of the annular or tubular graft material forms a substantially sinusoidal shape.

Still another aspect of the present invention may be an expandable annular joining member for joining first and second hollow structures during creation of an anastomosis, such as an end-to-side anastomosis, using an anastomosis device. The joining member may include a plurality of interconnected loops forming an annular body and a plurality of joining elements for joining the hollow structures. The joining member also includes a plurality of joining elements for joining the hollow structures connected to the annular body at locations where adjacent loops are interconnected to each other, and wherein the loops are configured to permit radial expansion of said annular body to expand said joining member from a first position to a second position having a second, larger diameter than the first position.

Another aspect of the present invention may be a method for providing access to a hollow structure located inside a mammalian body for an endoluminal repair device having a delivery part. The method may include steps of:

providing a prosthetic graft of sufficient length for one end to reach said hollow structure through an opening in the body while a second proximal end of said graft remains outside the body, creating an anastomosis between the prosthetic graft and said hollow structure in a manner whereby fluid can flow from said hollow structure through said prosthetic graft, advancing said endoluminal repair device from outside the body through the prosthetic graft to a location where at least a part of said delivery part of said endoluminal repair device is located in said hollow structure, deploying said delivery part of said endoluminal repair device, retracting said endoluminal repair device outside the body, closing said prosthetic graft at a site inside the hollow structure; and cutting and removing the remainder of said prosthetic graft after said closing step.

The invention will be further illustrated by the specific embodiments described below which are not to be construed as limiting the invention in any way. The scope of the invention is to be determined by the claims appended hereto.

DETAILED DESCRIPTION OF THE PREFERRED EMBODIMENT(S)

Figure 1:
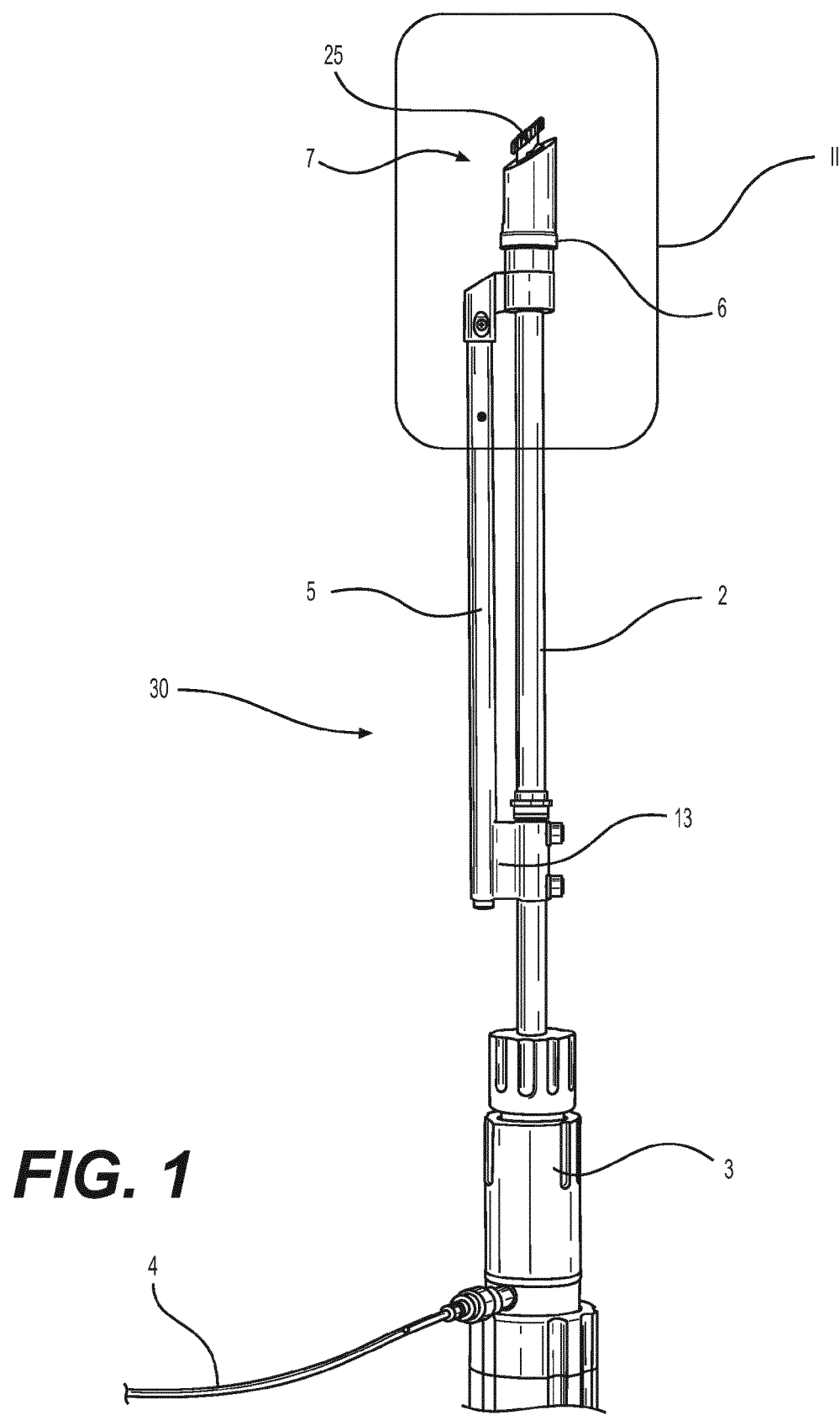
FIG. 1 is a side view of an embodiment of an applicator of the anastomosis device.

For illustrative purposes, the principles of the present disclosure are described by referencing various exemplary embodiments.

The present invention relates to an anastomosis device for creating an anastomosis between structures. The anastomosis device includes three components, a joining member used for joining the structures and supporting and maintaining the anastomosis, an applicator for deploying the joining member and an actuator for actuation of movements of the applicator to deploy the joining member.

Preferred embodiments of the invention will now be described in detail. The detailed description below shows embodiments of the device adapted for making an approximately 60° angled anastomosis between a prosthetic vascular graft and the ascending aorta during surgery for connecting the arterial side of an implantable cardiac assist device. A take-off angle of the prosthetic vascular graft relative to the aorta being substantially smaller than 90° is desirable in order to avoid kinking due to the anatomical constraints inside the thoracic cavity. This take-off angle is also advisable in a wide variety of other vascular anastomosis procedures. This example is given by way of illustration only and is not meant to limit the invention. Persons skilled in the art will recognize that the devices, auxiliary devices and methods of the present invention are readily adaptable to other types of anastomoses.

For the purpose of the description, the distal end of the applicator or device refers to the end of the applicator or device that is designed for positioning at the location of the anastomosis site and the proximal end of the applicator or device refers to the end of the applicator or device designed for positioning away from the location of the anastomosis site.

In one embodiment of the anastomosis system, the applicator includes a tubular member, comprising an expander, a longitudinally slit, expandable outer tube and a longitudinally slit, expandable inner tube providing a seat for the joining member, and a mechanism for causing a special sequence of movements for expansion and deformation of the joining member. This sequence comprises an axial movement of the expander relative to the outer and inner tubes to radially expand the joining member, followed by an axial movement of the outer and inner tubes relative to each other to deform the joining elements. These movements are then reversed to return the applicator to the original, unexpanded state in order to allow the applicator be removed from the anastomosis site. One embodiment of such a mechanism comprises at least a spring to modify one axial movement into the required sequence of movements, as described previously, for example, in US 2009/0112304 A1.

The joining member comprises an annular or tubular element and a plurality of joining elements. Alternatively, the joining member may comprise separate joining elements only. The seat of the tubular member is adapted to hold and position the joining member, such that the main plane of the joining member is angled relative to the longitudinal axis of the tubular member. The main plane of the distal end of the tubular member of the applicator is substantially parallel to the main plain of the joining member in order to minimize the length of the part of the tubular member that needs to be inserted into the lumen of the structure to be joined. The expander is shaped to comply with the angle of the main plane of the joining member relative to the longitudinal axis of the tubular member.

Upon actuation, the expander causes radial expansion of the outer and inner tubes of the applicator. This expansion causes the main plane of the seat, holding the joining member, to rotate from, for example, about a 45° angle, relative to the longitudinal axis of the tubular member, to a larger angle, in this embodiment by design being about 60°. The distal end of the prosthetic vascular graft is cut at a similar angle, such that the bevelled end fits precisely to the hollow structure at the intended 60° angle. The use of different vascular graft take-off angles may require corresponding, different angles of the main plane of the seat, relative to the longitudinal axis of the anastomosis device, and a corresponding adaptation of the bevel of the prosthetic vascular graft.

To realize the specific sequence of movements required to create the anastomosis, certain embodiments of the applicator include a mechanism that includes at least a spring to modify a single axial movement into the required sequence of movements, as described previously, for example, in US 2009/0112304 A1. This sequence of movements comprises an axial movement of the expander relative to the applicator to radially expand the joining member, and an axial movement of the inner and outer tubes relative to each other to deform the joining elements of the joining member to the joining position.

Now referring to FIG. 1, one embodiment of an applicator 30 is shown. Applicator 30 includes a tubular member 2 which may be, for example, a metallic annular or tubular member, although other suitable sterilizable materials having sufficient rigidity may be employed. A grip 3 is provided at a proximal end of tubular member 2. Grip 3 is provided for holding the anastomosis device during use thereof. In this embodiment, grip 3 also houses an actuator (not shown).

Still referring to FIG. 1, a preferably flexible tube 4 is connected to grip 3. Tube 4 leads to a controller (not shown) for controlling components of actuation section 7 provided at a distal end of the tubular member 2 of applicator 30. The actuator of applicator 30 may be mechanical, electrical, pneumatic or hydraulic. The controller used with applicator 30 shown in FIG. 1 may, for example, be a syringe connected to tube 4. The syringe is used for introducing a fluid into actuator 30 or withdrawing a fluid from applicator 30, in order to control movement of the components of actuation section 7. Alternatively, tube 4 may hold a flexible wire for use with a mechanical controller. Suitable controllers and corresponding actuation mechanisms for use in the present invention are described, for example, in US 2009/0112304 A1.

Applicator 30 is provided with a support member that is attached to tubular member 2. The support member includes a support rod 5, tubular part 6 and an attachment 13 for attaching the support member to tubular member 2. Attachment 13 may be located proximate to grip 3. The support member should be attached to tubular member 2 of actuator 30 at a position remote from actuation section 7. In use, applicator 30 is employed to actuate joining member 15 to create an anastomosis between first and second hollow structures.

As used herein "hollow structure" refers to either a graft material or a blood vessel. The first hollow structure typically refers to the hollow structure located in a body to which a second hollow structure 8 (FIG. 2) will be joined by the anastomosis. Second hollow structure 8 generally refers to a graft hollow structure that is delivered to the site of the anastomosis by the applicator and attached to the first hollow structure during creation of the anastomosis.

Figure 2:
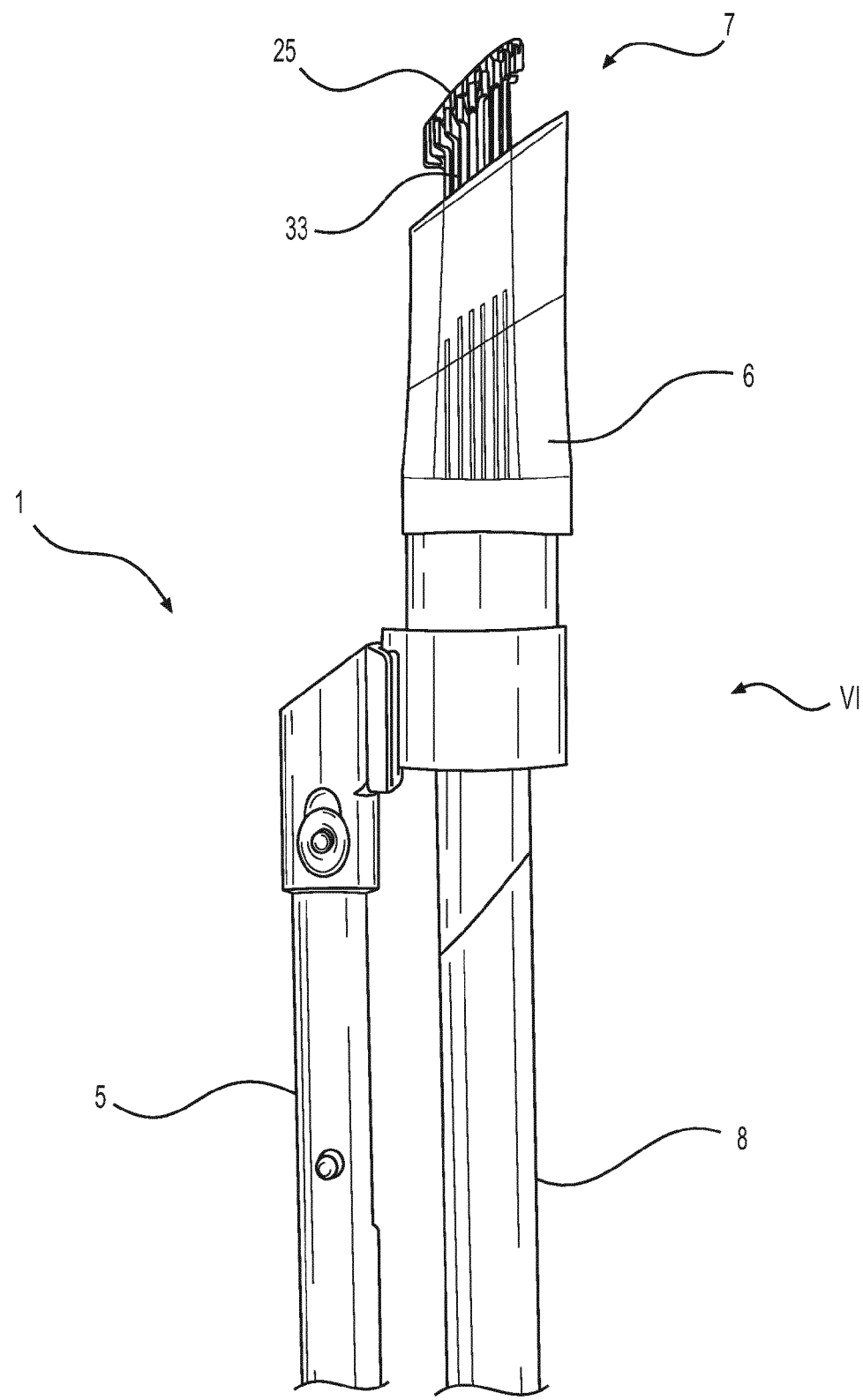
FIG. 2 is an expanded view of section II of the applicator shown in FIG. 1 with a graft vessel positioned thereon (the "actuation position").
Figure 6:
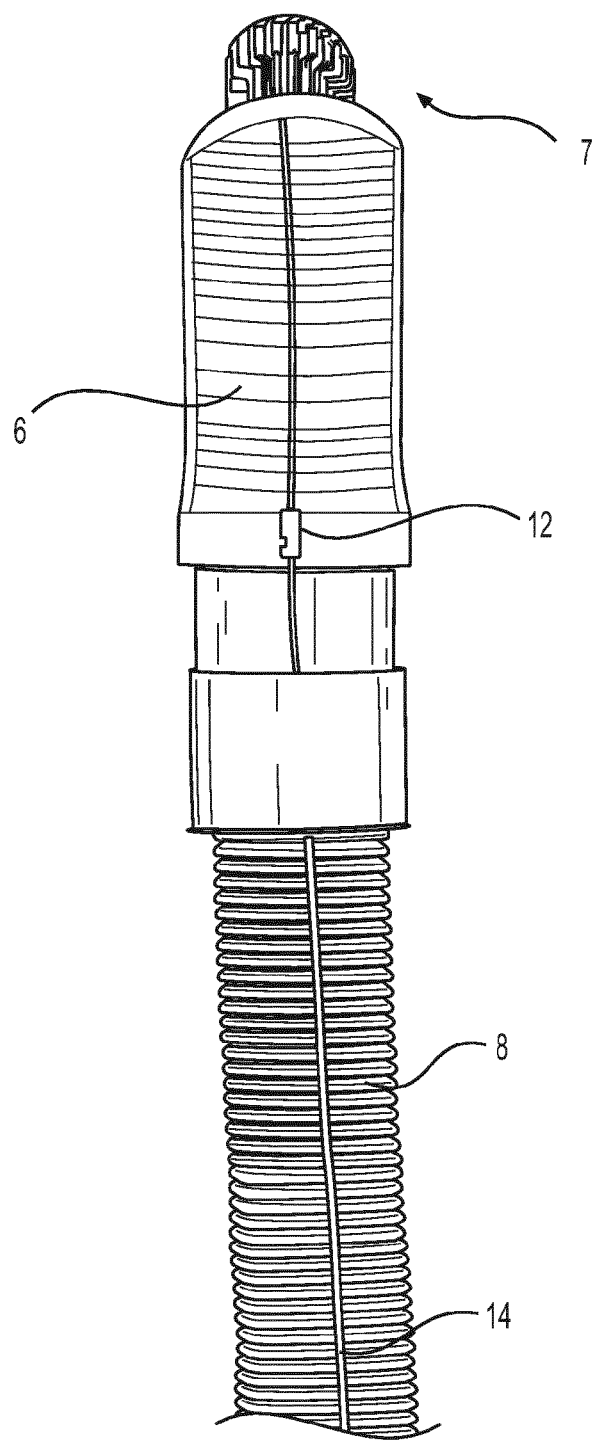
FIG. 6 is a side view of the applicator shown in FIG. 2 with the graft vessel positioned thereon.

In use, tubular member 2 and actuation section 7 are inserted into second hollow structure 8, as shown in FIGS. 2 and 6. It is, therefore, desirable to attach the support member to tubular member 2 at a position sufficiently remote from actuation section 7 so as not to interfere with insertion of tubular member 2 and actuation section 7 into second hollow structure 8. By attaching support rod 5 of the support member to tubular member 2 using attachment 13 in the manner shown in FIG. 1, introduction of tubular member 2 into the second hollow structure 8 is not hindered by either attachment 13 or support rod 5. Tubular member 2 can thus be inserted through the entire length of second hollow structure 8 such that actuation section 7 may extend out from the distal end of second hollow structure 8, as shown in FIGS. 2 and 6. Attachment 13 may be a permanent attachment or a releasable attachment as shown in the depicted embodiments. Attachment 13 may be par-axial with tubular member 2 as shown in FIG. 1 or, alternatively, attachment 13 may be constructed differently, for example coaxial to tubular member 2.

Applicator 30 further comprises a tubular part 6, which is configured be placed around the periphery of tubular member 2, as shown in FIG. 1. Tubular part 6 of applicator 30 is placed substantially co-axially or co-axially with respect to the longitudinal axis of tubular member 2. Tubular part 6 is attached to support rod 5 which is further attached to tubular member 2 by attachment 13 as discussed above. Tubular part 6 may be disconnected from the support member, in order to remove tubular part 6 from actuator 30 or for placement of tubular part 6 onto applicator 30. It is possible to remove tubular part 6 from tubular member 2 and hollow structure 8 by disconnecting tubular part 6 from support rod 5 and longitudinally splitting tubular part 6 to allow tubular part 6 to be spread open and removed from tubular member 2 and hollow structure 8 in a substantially radial direction.

In one embodiment, tubular part 6 is a stiff tubular part adapted to closely surround at least part of the distal end of second hollow structure 8 (the prosthetic vascular graft). The shape of the distal end of tubular part 6 is adapted to correspond substantially to the shape of the distal end of second hollow structure 8. For example, in case of a bevelled vascular graft, tubular part 6 is also bevelled. By providing radial stiffness, tubular part 6 exerts an inwardly directed radial counterforce on the bevelled distal end of the prosthetic vascular graft against the outwardly directed radial deformation force transmitted by joining member 15 during actuation of the anastomotic system. This is advantageous since joining member 15 is deformed substantially radially outwardly upon actuation from a first diameter to a second, larger diameter, causing joining elements 18 of joining member 15 to engage the prosthetic vessel wall from the inside of the prosthetic vessel and to pass through and out of the prosthetic vessel wall on the outside of the prosthetic vessel.

It is desirable that the joining elements 18 penetrate the wall of the prosthetic vascular graft. However, it has been found in prior art devices that depending on the elasticity of the prosthetic graft material and on the angle of the bevel of its distal end, the joining elements 18 may just push away the prosthetic graft material without penetrating the material as desired. In the present invention, due to the radial support provided proximate to the distal end of the prosthetic vascular graft, the wall of the graft vessel is held firmly in place during radial expansion of joining member 15, ensuring that the joining elements 18 penetrate the wall of the graft vessel.

Tubular part 6 is configured to constrain the distal end of the prosthetic vascular graft. Attachment of tubular part 6 to support rod 5 ensures proper orientation of tubular part 6 relative to the main plane of joining member 15 both axially and rotationally, and facilitates precise positioning of the prosthetic vascular graft relative to joining member 15 when preloading applicator 30.

As shown in FIG. 2, second hollow structure 8 may be a graft structure. The graft structure may be any material suitable for vessel grafts having suitable properties for the particular intended use. Graft material may be, for example, a fabric material or the like. Second hollow structure 8 is placed over tubular member 2 and within tubular part 6 of applicator 30 for delivery to the anastomosis site. Tubular part 6 of applicator 30 encloses second hollow structure 8 and is able to temporarily retain second hollow structure 8 at a desired position relative to tubular member 2. The second hollow structure 8 of graft material may be folded to an accordion shape to allow limited extension of the graft material by unfolding or straightening of the folded section (s). Tubular part 6 may be provided with a circumferentially ribbed section on an inner surface thereof (not shown) in order to provide frictional engagement with the accordion-shaped graft material.

Also shown in FIG. 2, the actuation section 7 comprises a seat 33 adapted for holding a joining member 15 and for positioning the joining member 15 proximate to a distal end of second hollow structure 8 of graft material. Actuation of joining member 15 by means of the actuation section 7 of actuator 30 is described below. The plane of the proximal end of seat 33 of actuation section 7 is not parallel with the plane of the distal end of tubular part 6 in the first, unexpanded position of actuator 30.

Figure 12A:
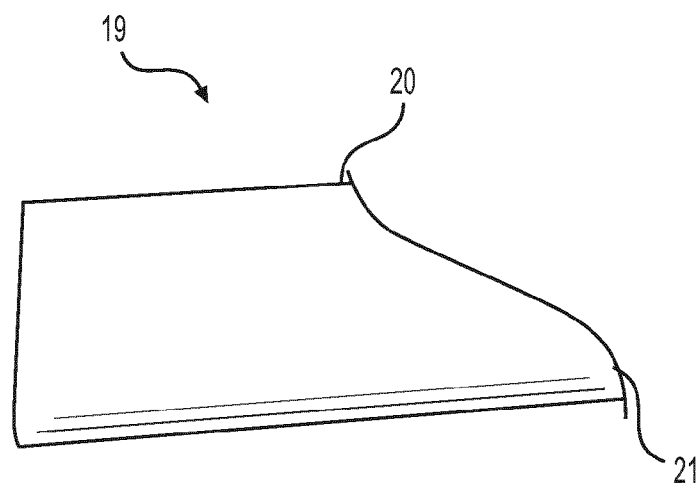
FIG. 12A shows the contour of a template that may be used for cutting a graft material to provide a graft vessel.

Tubular part 6 of the support member provides radial stiffness to the graft material proximate to the distal end thereof. Since the graft material is cut at an angle at a distal end thereof, the radial stability is reduced relative to a material that is not cut an angle. The radial stability is reduced, in particular, at the toe 21 of the distal end of the graft material, as shown in FIG. 12A. Thus, the graft material requires additional support at the distal end, which support is provided by tubular part 6 of the support member.

Figure 3:
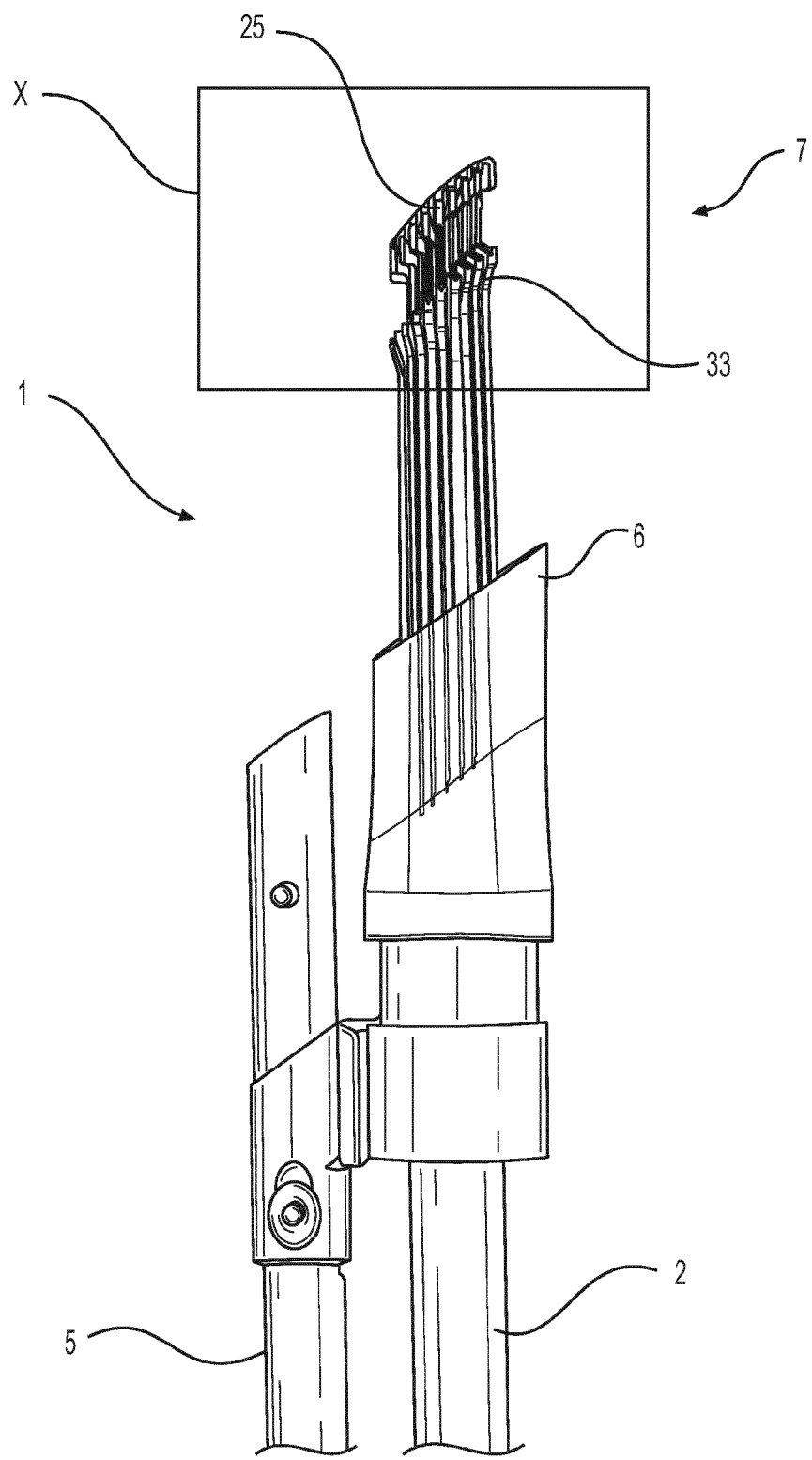
FIG. 3 is a view of the applicator shown in FIG. 2 in a first insertion/removal position (the "viewing position").

FIG. 3 differs from FIG. 2 in that no graft material of the second hollow structure 8 is shown in position on the device, and tubular part 6 is shown connected to support rod 5 and tubular member 2 in a different position, i.e. a viewing position. In this viewing position, tubular part 6 has been retracted away from the actuation section 7 in an axial direction such that a user of applicator 30 has a clear view of seat 33 of actuation section 7 and thus joining member 15. It is, therefore, possible for the user to position joining member 15 within the first hollow structure without hindrance from tubular part 6 when tubular part 6 is in this retracted position.

Figure 4:
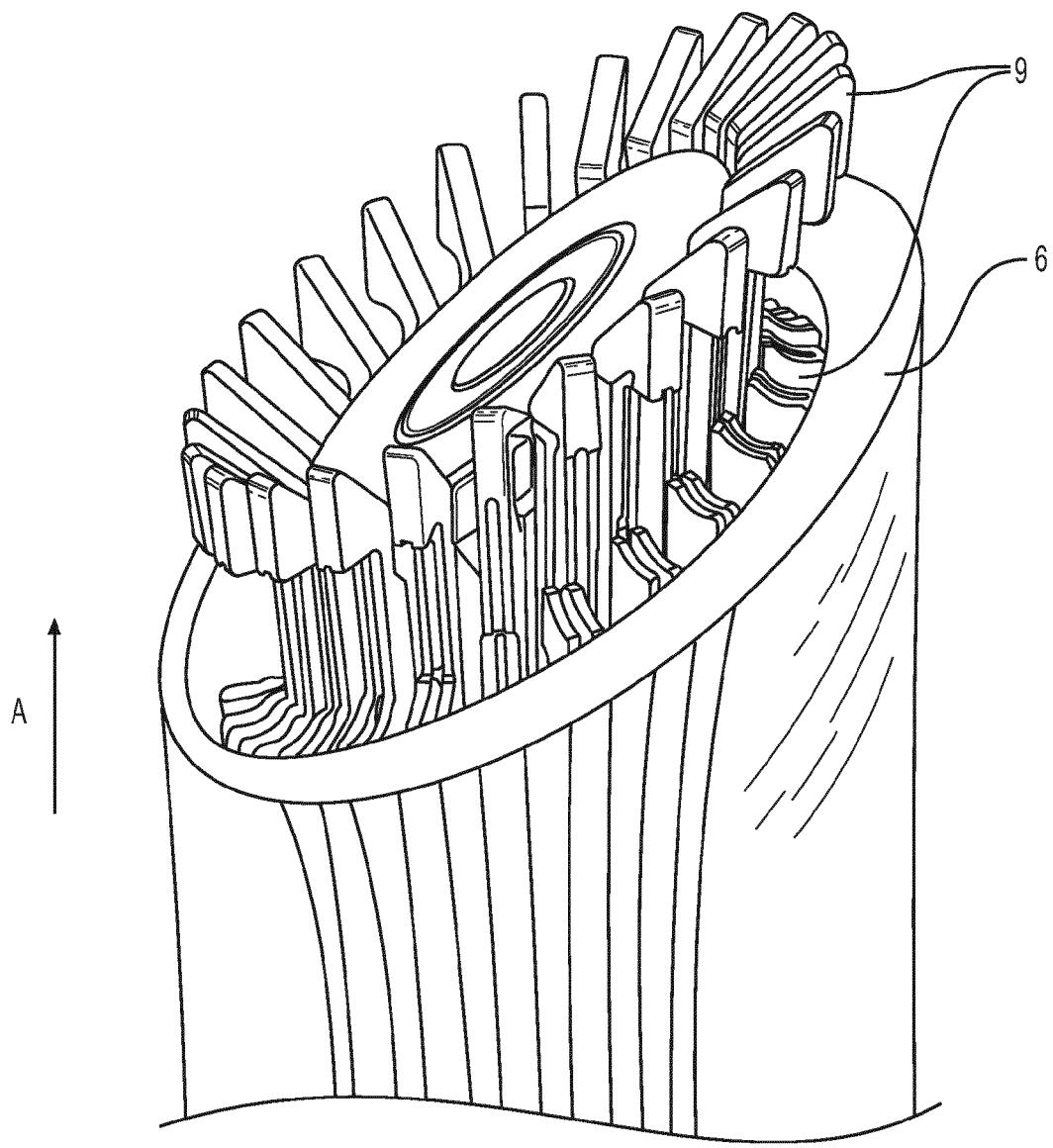
FIG. 4 is an enlarged view of the seat of the applicator of FIG. 1 when the applicator is in an expanded state during creation of the anastomosis.

In FIG. 4, actuation section 7 is shown in an expanded state. Tubular part 6 has been moved to the actuation position. The actuation position is characterized by a precise alignment of the distal end of hollow structure 8, held in place by tubular part 6, relative to actuation section 7 of applicator 30. A plane defined by the proximal end of seat 33 of actuation section 7 is parallel with the plane of the distal end of tubular part 6 in this expanded position of actuation section 7. This is caused by a change in the angle of the main plane of seat 33 that occurs during expansion of actuation section 7, namely, the angle of seat 33 relative to the longitudinal axis of actuator 30 is increased, in this case from 45° to 60°.

FIG. 4 also shows that actuation section 7 comprises two sets of anvils 9, and may be moved both axially and radially with respect to the longitudinal axis of tubular member 2. Joining member 15 which may be placed onto seat 33 of actuation section 7 is expanded by radially expanding seat 33. Anvils 9 are also moved radially with seat 33. Joining member 15 is then in the second, expanded position. Subsequently, proximal anvils 9 may be moved in direction A towards distal anvils 9 for actuating joining member 15 in a direction parallel to the longitudinal axis of tubular member 2. Thereafter, joining member 15 is in a third joining position in which the hollow structures are joined. For a further explanation of the operation of the actuation section 7 and joining member 15, reference is made to WO 02/38055.

Figure 5:
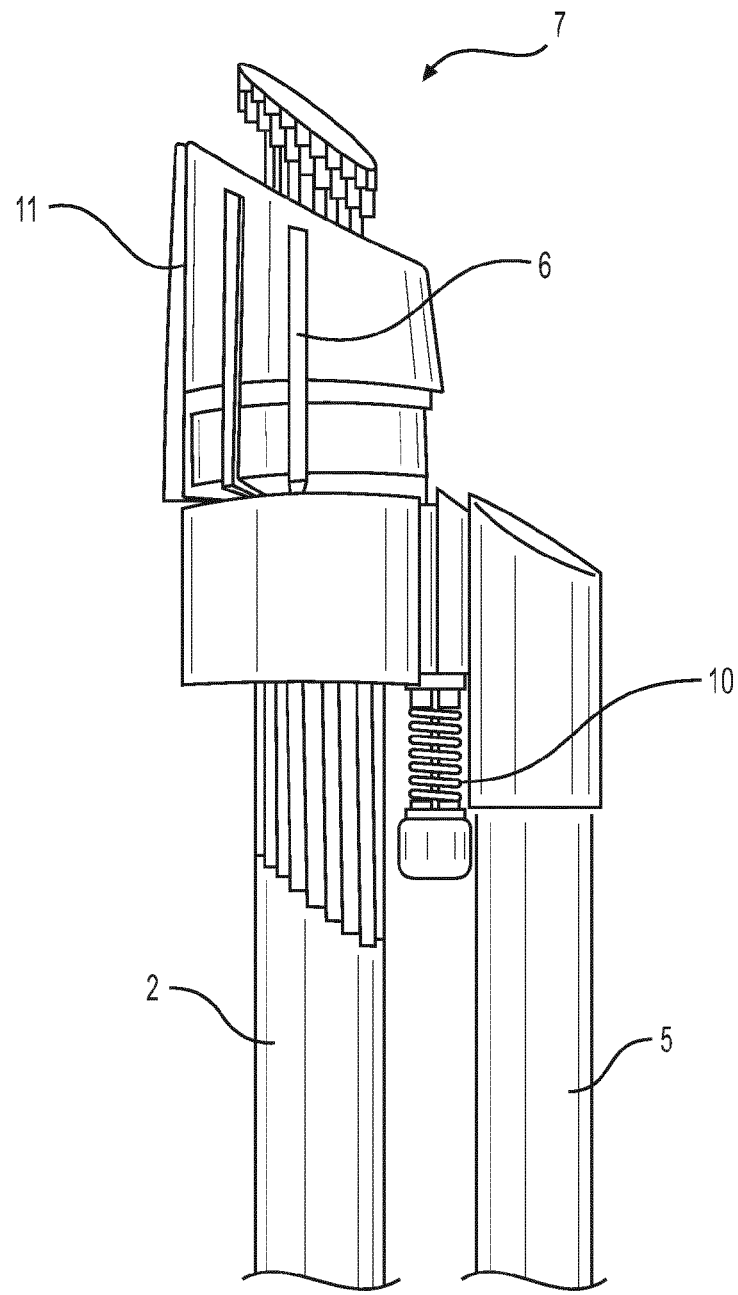
FIG. 5 is a side view of an alternative embodiment of a distal portion of the applicator.

FIG. 5 shows an alternative embodiment of applicator 30. In this embodiment, tubular part 6 comprises a radial stiffener 11 and a compliant element 10. Radial stiffener 11 comprises interconnected fingers extending around tubular part 6 of the support member. Radial stiffener 11 provides additional radial stiffness to tubular part 6 and therefore to second hollow structure 8 (not shown here) proximate to the distal end thereof. One purpose of radial stiffener 11 is to assure that the joining elements 18 of joining member 15 penetrate the second hollow structure 8. Also, in the case that the first hollow structure is an aorta, joining occurs independently of the counter pressure exerted by the aorta on the second hollow structure 8.

The compliant element 10 provides axial compliance to at least tubular part 6 of the support member with the second hollow structure 8, in particular during joining of the hollow structures. In this embodiment, the compliant element 10 is formed by a spring positioned in the connection between tubular part 6 and support rod 5. The compliant element 10 may also be formed by means of the provision of a specific shape of the connection between tubular part 6 and support rod 5. It is, for example, possible to produce the support member from plastic and it is known that certain plastics when fabricated in specific shapes may have resilient properties. Compliant element 10 allows limited axial movement of at least part of the support member relative to tubular member 2, for example about 0.5-2.0 mm of axial movement of at least part of the support member relative to tubular member 2 is permitted. Small movements of the joining member 15 relative to the support member in the axial direction may occur, for example, when only the inner tube moves in axial direction relative to the support member during actuation of joining member 15. Since joining member 15 grasps the wall of the aorta and the distal end of tubular part 6 is circumferentially in contact with the outer surface of the wall of the aorta, any movement of joining member 15 relative to tubular part 6 is transmitted to the wall of the aorta. The advantage of an axially compliant element 10 is that it can absorb this axial movement and thereby prevent the force from being transmitted to the outer wall of the aorta or avoiding losing touching contact between tubular part 6 and the aorta during the process of creating the anastomosis. One way to achieve axial compliance is, for example, to include a spring in the applicator 30.

FIG. 6 shows an orientation element 12 for orienting second hollow structure 8 relative to tubular part 6. As can be seen in FIG. 2, it is important that tubular part 6 and the graft material of second hollow structure 8 be oriented correctly in the circumferential direction due to the nonsymmetric shapes of their respective distal ends. Otherwise, tubular part 6 will not provide radial stiffness proximate to the distal end of the graft material of second hollow structure 8 around the entire circumference of the graft material. Since commercially available graft material is provided with a marking line 14 visible from the outside which may be used for orienting the graft material of second hollow structure 8, an orientation element 12 in the form of a marker on the outer surface of tubular part 6 may be used in conjunction with marking line 14 for orienting the graft material with respect to tubular part 6. A user of the anastomosis device is then able to properly orient a commercially available graft material for creating the anastomosis. Commercially available graft material does not have a distal end having the shape of the distal end of the graft material of the hollow structure 8 described in this application and thus must be cut to this shape as described below.

Figure 7:
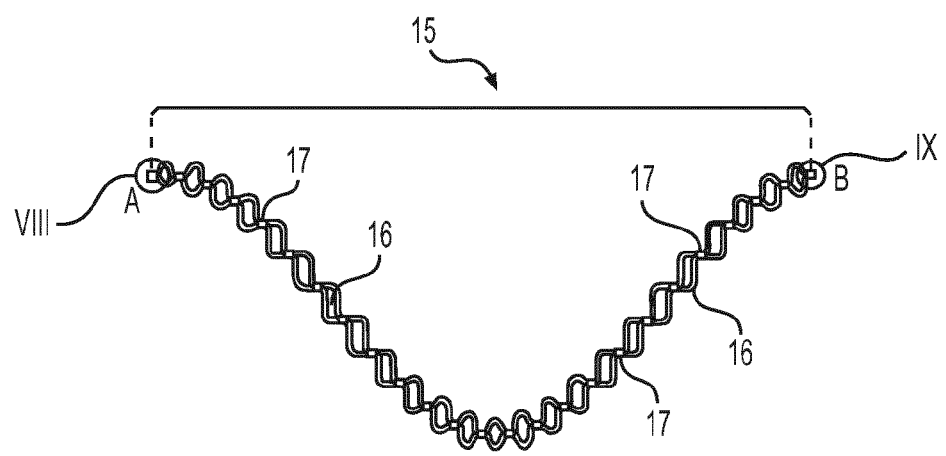
FIG. 7 is a view of a joining member which has been cut through one of the loops.
Figure 8:
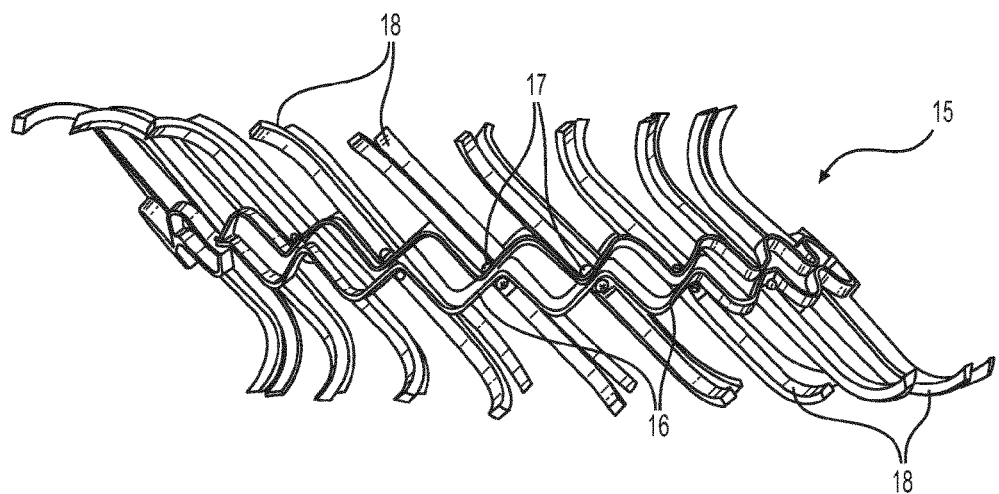
FIG. 8 is view of the joining member shown in FIG. 7 in the first, unexpanded position.
Figure 9:
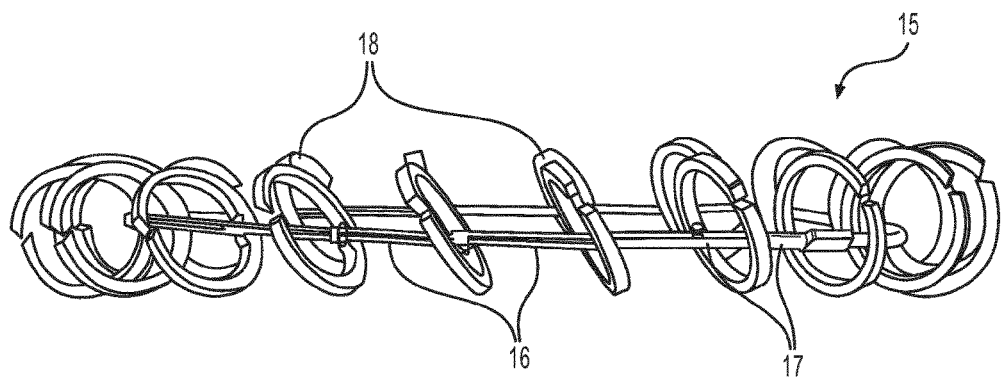
FIG. 9 is a view of the joining member shown in FIG. 8 in the second, expanded or fired position.

FIG. 7 shows joining member 15 cut at one location along the length of joining member 15. Joining member 15 comprises a plurality of loops 16 each interconnected with adjacent loops 16 by means of connecting elements 17 to form an annular element or ring as can be seen in FIG. 7. Connecting elements 17 provide attachment locations for attaching the joining elements 18 shown in FIGS. 8-9.

The joining elements 18 are in the form of staples which may be actuated in a direction parallel to the longitudinal axis of tubular member 2, i.e. axially contracted when joining member 15 is positioned on seat 33 of applicator 30. The axial contraction of the staples of joining member 15 closes the staples to establish a joint between the first and second hollow structures. For a further explanation of the operation of the joining member 15, reference is made to WO 02/38055.

Depending on the anastomosis geometry, however, the system discussed above may have certain limitations. For example, in the case of an end-to-side anastomosis wherein the longitudinal axes of the first and second hollow structures are at an angle smaller than 90°, joining member 15 may fail to properly engage part of the wall of the bevelled end of the second hollow structure 8 during creation of the anastomosis. This phenomenon is caused by insufficient radial stability of the distal end of the bevel of the second hollow structure 8, i.e. the toe 21. As a result, the anastomosis may immediately leak or may be weakened and may disintegrate upon movement or exertion of force thereon.

Use of the anastomosis device is described herein for creation of an anastomosis at a 60° take-off angle between a prosthetic vascular graft and the ascending aorta during surgery for connecting the arterial side of an implantable cardiac assist device. A take-off angle of the prosthetic vascular graft relative to the aorta substantially smaller than 90° is desirable. By employing a take-off angle between approximately 45° and 75° kinking due to anatomical constraints inside the thoracic cavity can be avoided in actual practice. Smaller angles than 45° lead to impractical anastomoses due to a resultant elongated oval shape at the connection. Material compliance generally allows a slight bend in hollow structure 8, sufficient to reach angles smaller than 45°, if required. Similarly, use of a take-off angle between approximately 45° and 75° is also advisable in a wide variety of other vascular procedures. The exemplary anastomosis used to illustrate the present device and method is used for illustration only and is not meant to limit the scope of the invention in any way. Skilled persons will recognize that the anastomosis devices, auxiliary devices and methods of the present invention are readily adaptable to other types of anastomoses in addition to the one described above.

In an embodiment of the anastomosis device, the device includes a tubular member 2, comprising an expander, a longitudinally slit, expandable outer tube and a longitudinally slit, expandable inner tube providing a seat 33 for joining member 15, and a mechanism for causing a special sequence of movements for expansion and deformation of joining member 15. This sequence of movements comprises an axial movement of the expander relative to the outer and inner tubes to radially expand joining member 15 from a first position to a second, expanded position, followed by an axial movement of the outer and inner tubes relative to each other to deform the joining elements 18 to a joining position. This sequence of axial movements is then reversed to return the applicator 30 to its original, unexpanded first position to facilitate removal of the device from the anastomosis site.

An embodiment of a mechanism suitable for imparting this sequence of movements may comprise at least one spring in order to convert a single axial movement to provide the required sequence of movements, as described, for example, in US 2009/0112304 A1 in order to simplify use of the device.

Joining member 15 comprises an annular or tubular element and a plurality of joining elements 18. Alternatively, joining member 15 may comprise only a set of a plurality of separate joining elements 18. Tubular member 2 is adapted to hold joining member 15, such that the main plane of joining member 15 is maintained, for example, at about a 45° angle relative to the longitudinal axis of tubular member 2. The plane of the distal end of tubular member 2 of applicator 30 is thus oriented substantially parallel to the main plane of joining member 15 in order to minimize the length of the part of tubular member 2 that must be inserted into the lumen of the aorta for creation of the anastomosis.

The expander is also asymmetric so as to conform to the angle of the main plane of joining member 15 relative to tubular member 2. In one embodiment, the expander is a skewed cone having an oval base plane with grooves on the cone that match with the angled ends of the slitted inner tubular member 2. Upon actuation, the expander causes the outer and inner tubes to expand in a radial direction. This expansion causes the main plane of seat 33 supporting joining member 15, to rotate from about a 45° angle, relative to the longitudinal axis of tubular member 2, to a larger angle, which, in this embodiment is about a 60° angle. The distal end of the prosthetic vascular graft is cut at a similar angle of about 60°, such that the bevelled distal end of the graft fits precisely to the aorta at the intended 60° angle. Different vascular graft take-off angles may require corresponding, different angles of the main planes of seat 33, relative to the longitudinal axis of actuator 30 and the bevelled distal end of the prosthetic vascular graft.

One way to retain the prosthetic vascular graft on applicator 30 is by clamping. Clamping can be achieved by closely surrounding at least part of the prosthetic vascular graft with a structure such as tubular part 6 which forms a part of applicator 30. The inner surface of tubular part 6 of applicator 30 may be textured to increase friction between this inner surface and the prosthetic vascular graft. Many commercially available prosthetic grafts feature a transversally ribbed, accordion-shaped outer surface. In one embodiment, a corresponding ribbed section is provided on an inner surface of at least the distal portion of tubular part 6. Thus, applicator 30 may be sized to closely enclose the outer surface of the prosthetic vascular graft with minimal or no clearance there between in order to increase the resistance of the vascular graft against axial movement.

In order to facilitate loading of the prosthetic vascular graft onto applicator 30 and removing applicator 30 from the anastomosis site upon completion of the anastomosis, it may be advantageous that the support member be detachable from applicator 30. Applicator 30 may, for example, be first positioned proximate to the distal end of the prosthetic vascular graft. Next, tubular part 6, holding the prosthetic vascular graft (the second hollow structure 8), may be attached to a predefined attachment site on applicator 30 by way of an attachment 13, such that the distal end of the prosthetic vascular graft is automatically located at an optimal position relative to joining member 15. After completion of the anastomosis, the support member may be detached from applicator 30 in order to facilitate withdrawing applicator 30 from the prosthetic vascular graft.

Applicator 30 may include means to easily release the prosthetic vascular graft in order to facilitate removal of applicator 30 after completion of the anastomosis. In one embodiment, this is achieved by including a means to split tubular part 6 of applicator 30 longitudinally, thereby effecting immediate termination of any clamping properties of tubular part 6 on the prosthetic vascular graft which releases the prosthetic vascular graft from applicator 30. In a preferred embodiment, this is achieved by fabricating tubular part 6 from at least two parts and providing a releasable attachment mechanism to hold the at least two parts of tubular part 6 together. The at least two parts of tubular part 6 may be spring loaded to facilitate easy release of the attachment. Alternatively, tubular part 6 may, for example, be constructed from a suitable plastic that includes a longitudinal line of weakness that facilitates splitting by tearing along the longitudinal line of weakness. In one embodiment a longitudinal groove in the outer surface of tubular part 6 provides a line of weakness for splitting tubular part 6.

An advantage of this embodiment is that it enables removal of tubular part 6 from the prosthetic vascular graft without requiring axial movement of the support member relative to the prosthetic vascular graft. This frees up applicator 30 to be easily removed from the anastomosis site. Easy removal of applicator 30 after completion of the anastomosis is desirable in order to avoid excessive force or traction on one or both of the first and second hollow structures that may cause damage to or leaking of the anastomosis.

In another embodiment, the applicator 30 may be provided with a means that enables limited radial compliance of tubular part 6. This may be advantageous to avoid excessive forces between joining member 15 and tubular part 6 during actuation of the anastomosis device. Since the actuation of joining member 15 includes a radially outward movement of the joining elements 18, the joining elements 18 may push against the inside of tubular part 6. One purpose of tubular part 6 is to support the distal end of the prosthetic vascular graft to facilitate wall penetration by the joining elements 18. Thus, the distal end of tubular part 6 may be fabricated to be sufficiently stiff to fulfil this purpose, but may still be able to yield to stronger forces which may be caused by the radially outward movement of the joining elements 18 upon actuation of the anastomosis device. Tubular part 6 of applicator 30 may yield, for example, by a slight radially outward movement responsive to excessive force exerted on tubular part 6 by moving joining elements 18 during radial expansion. One way to achieve such a controlled compliance is by careful selection of a material with suitable material properties, such as certain types of plastic tubing, for example silicone. Another way to achieve this is to provide the distal end of tubular part 6 with longitudinal slits, folds or grooves that enable some radial expansion responsive to a force that exceeds a predetermined threshold level.

Tubular part 6 may be moveable between two or more positions relative to joining member 15, seated on tubular member 2 of applicator 30, namely, (1) a viewing position, in which the distal end of tubular part 6 of applicator 30 has been moved away from the distal end of the tubular member 2, offering the user an unimpeded view of the distal end of tubular member 2 for positioning joining member 15 in the first hollow vessel for the anastomosis process, and (2) an actuation position, in which tubular part 6 is moved distally relative to applicator 30 in order to align tubular part 6 with joining member 15. This embodiment has the advantage that a user may be provided with a good view for accurately positioning joining member 15 in a desired position. Thereafter, applicator 30 can be moved to the actuation position for making the anastomosis.

Methods of creating an anastomosis are now described. Use of the anastomosis device and methods of the present invention, a variety of different types of anastomoses, including end-to-side anastomoses may be performed using minimally invasive procedures.

To create an end-to-side anastomosis, a surgeon must obtain access to the anastomosis site, e.g., the arcus aortae or the aorta descendens of the patient, referred to herein as the first hollow structure. The take-off angle for the anastomosis must be determined.

Then, based at least in part on the distance into the body that must be traversed to reach the anastomosis side, the graft material of the second hollow structure 8 is cut to length. Subsequently, the end of the graft material of second hollow structure 8 destined for use as the distal end is cut at an angle to substantially match the take-off angle, i.e. it must not vary more than 15° and preferably not more than 5° from the take-off angle. Also, the edge of the distal end of the graft material of second hollow structure 8 is cut to the sinusoidal shape as discussed above. Thereafter, the second hollow structure 8 is associated with applicator 30 by insertion of tubular member 2 through the lumen of hollow structure 8 until the actuation section 7 of actuator 30 extends out from the distal end of the graft material of second hollow structure 8.

Once tubular member 2 is properly positioned relative to second hollow structure 8, tubular part 6 may be placed around the distal end of second hollow structure and a part of tubular member 2, in order to retain the second hollow structure 8 in position relative to tubular member 2. Applicator 30 is first set to the viewing position and, if necessary, joining member 15 is positioned on seat 33 of actuation section 7 at this time. Joining member 15 can be positioned on seat 33 earlier in the process, if desired, or the actuator may be provided with a preloaded joining member 15 if desired. The anastomosis device is then ready to be positioned at the anastomosis site.

Next, the anastomosis device is inserted into the body and positioned at the anastomosis site with distal anvils 9 of actuation section 7 extending into the aorta and oriented at the correct angle to provide the desired take-off angle. Once properly positioned, tubular part 6 of applicator 30 is moved axially to the actuation position. Then, joining member 15 is radially expanded by means of actuation of actuation section 7 from the first position to the second, expanded position. Subsequently, joining elements 18 of joining member 15 are deployed to the joining position by actuation of actuation section 7 from the second, expanded position to the third, joining position.

Once the graft material of second hollow structure 8 and the first hollow structure, namely, the aorta, are joined by deployment of the joining elements 18 to the joining position, applicator 30 is returned to the first, unexpanded position. Then, at least tubular part 6 may be opened by longitudinally splitting tubular part 6. When tubular part 6 is opened or otherwise separated from applicator 30, applicator 30 may be removed from the anastomosis site and the patient. The proximal end of the graft material of second hollow structure 8 may be connected to another structure such as an artificial heart. The final step in the surgical process is to close the incision used for obtaining access to the aorta by suturing.

The present invention further relates to a method of creating anastomosis between two hollow structures, such as an end-to-side anastomosis, by means of an annular joining member 15. The method includes at least the steps of inserting a tubular member 2 at least partly into a lumen of a second hollow structure 8, tubular member 2 having a seat 33 for supporting and retaining the joining member 15, positioning joining member 15 proximate to a distal end of second hollow structure 8, and actuating joining member 15 substantially radially relative to a longitudinal axis of tubular member 2 while providing radial support to second hollow structure 8 proximate to the distal end thereof, during actuation of joining member 15. The step of actuating joining member 15 may comprise a specific sequence of steps: a first step of expanding joining member 15 substantially radially relative to the longitudinal axis of tubular member 2 for bringing joining member 15 into a second expanded position, and a second step of actuating joining member 15 in a direction substantially parallel to the longitudinal axis of tubular member 2 for bringing the joining elements 18 of joining member 15 into a third joining position in which the two hollow structures are joined.

Using a preferred embodiment of the anastomosis device, the method of creating end-to-side anastomosis may include the following steps. The prosthetic vascular graft material (second hollow structure 8) is positioned and clamped inside the detached support member of applicator 30, such that the planes of the respective bevelled ends of the graft material and tubular part 6 correspond substantially. Tubular member 2 of applicator 30 is then inserted at least partially inside the prosthetic vascular graft and the support member is attached to applicator 30 and located in a viewing position, offering an unimpeded view of seat 33 on the distal end of tubular member 2 that holds joining member 15. In the viewing position, tubular part 6 is located closer to a proximal end of applicator 30 than when tubular part 6 if positioned in the actuation position.

Applicator 30 is then moved to the actuation position to precisely position the prosthetic vascular graft relative to joining member 15 for creation of the anastomosis. Next, applicator 30, with joining member 15 positioned on seat 33, is inserted into an appropriately sized hole in the wall of the aorta. Applicator 30 is then tilted in the plane of the bevel of the distal end of applicator 30, such that the main plane of the bevel corresponds substantially to a tangent plane of the aorta at the intended anastomosis site in order to provide the desired take-off angle. Next, applicator 30 is actuated and a mechanism carries out a specific sequence of movements by means of which joining member 15 is radially expanded relative to the longitudinal axis of tubular member 2 to the second, expanded position and then moved in a direction substantially parallel to the longitudinal axis of tubular member 2 for moving the joining elements 18 of joining member 15 to a third, joining position in which the prosthetic vascular graft and aorta are joined. Lastly, the mechanism reverses these movements and returns actuator 30 to the original, unexpanded state. The clamping mechanism of applicator 30 is then released, for example by longitudinally splitting and removing tubular part 6 of applicator 30 and the anastomosis device may then be withdrawn from the prosthetic vascular graft and removed from the anastomosis site.

One advantage of this embodiment of the device and method is that applicator 30 can be easily preloaded with the prosthetic vascular graft due to the provision of the detachable support member. Also, applicator 30 can be easily inserted into the prosthetic vascular graft and into the aorta in an unexpanded state. The features of the present invention improve the reliability of the anastomosis, since the joining elements 18 of joining member 15 are first positioned into close proximity of the walls of the first and second hollow structures before actuation of the joining member 15, and the angle of the distal end of tubular member 2, seat 33 and actuation section 7, as well as the angle of the distal end of second hollow structure 8 are closely adapted to the desired take-off angle thereby substantially improving the reliability of the anastomosis.

The present invention also relates to an expandable annular joining member 15 for joining hollow structures by anastomosis, such as end-to-side anastomosis, using an applicator 30 to deploy joining member 15. Joining member 15 includes a plurality of interconnected loops 16 each connected to two adjacent loops by a connecting element 17 in order to form an annular body. Joining member 15 also includes a plurality of joining elements 18 for joining first and second hollow structures. The joining elements 18 are connected to joining member 15 at connecting elements 17 which also connect adjacent loops 16. The interconnected loops 16 are configured to straighten to two parallel substantially straight elements upon actuation of joining member 15 by radial expansion thereof. Joining member 15 may be circular, elliptical or polygonal as viewed in its main plane. Joining member 15 is adapted for the two-step actuation method described in detail above.

Certain elements of joining member 15 are known from the patent publications mentioned above and especially from U.S. Pat. No. 6,966,917. One advantage of joining member 15 according to the present invention relative to the prior art devices is that the loops 16 provide a reliable means for radial expansion of joining member 15 by both providing slack in the joining member 15 which can be used for radial expansion while at the same time providing a pair of adjacent substantially parallel structural elements when radially expanded to the joining position that, taken together provide sufficient strength to minimize the chance of mechanical failure of the device during expansion and use.

Embodiments of joining member 15 of the present invention will now be described in detail in the context of an intended use with an anastomosis system for providing an end-to-side anastomosis between a prosthetic vascular graft and the ascending aorta at a 60° take-off angle. This description is premised upon actuation by an applicator 30 of the invention that is described above, though other types of applicators may be used.

Figure 10:
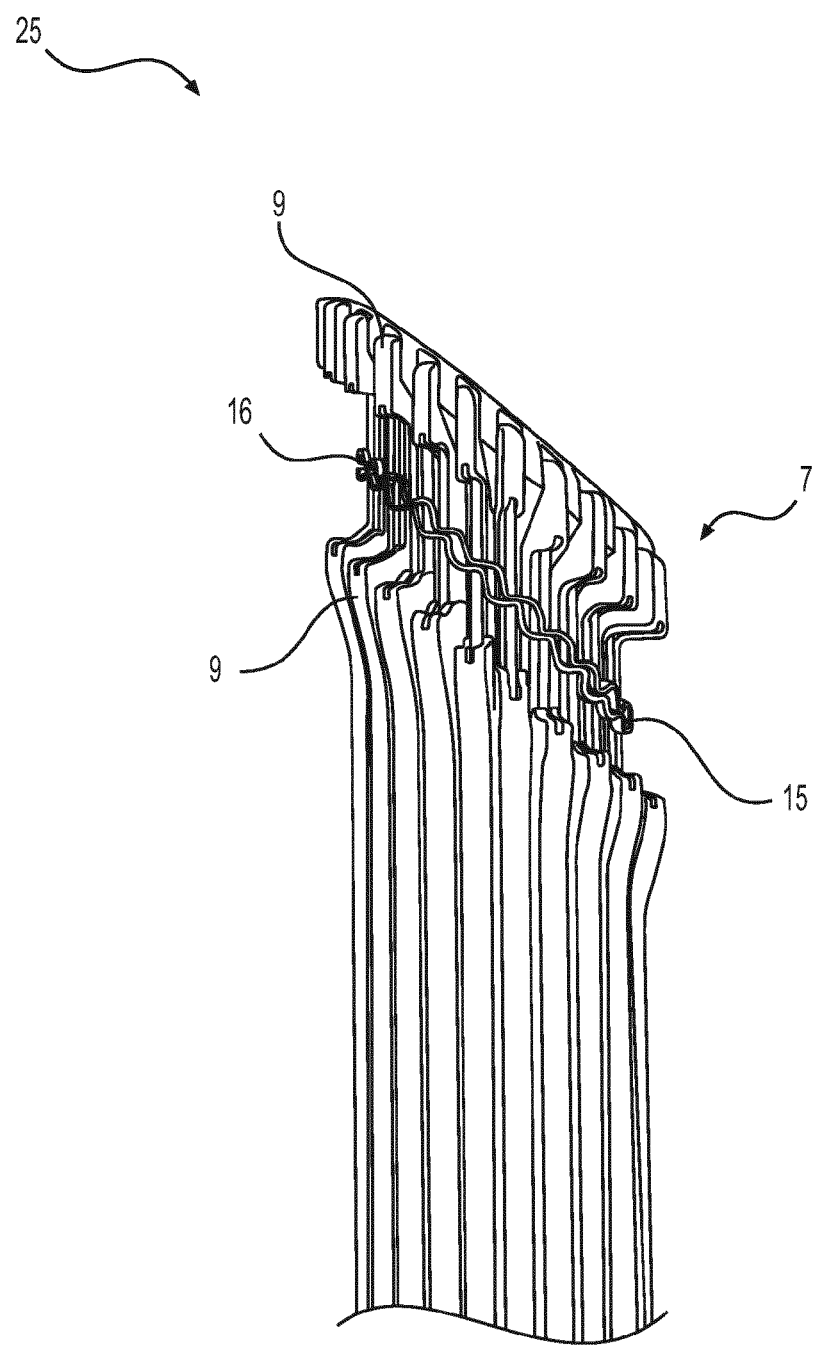
FIG. 10 is an expanded view of section X of the applicator shown in FIG. 3 seen from the opposite side as shown in FIG. 3 showing the applicator in the first unexpanded position.
Figure 11:
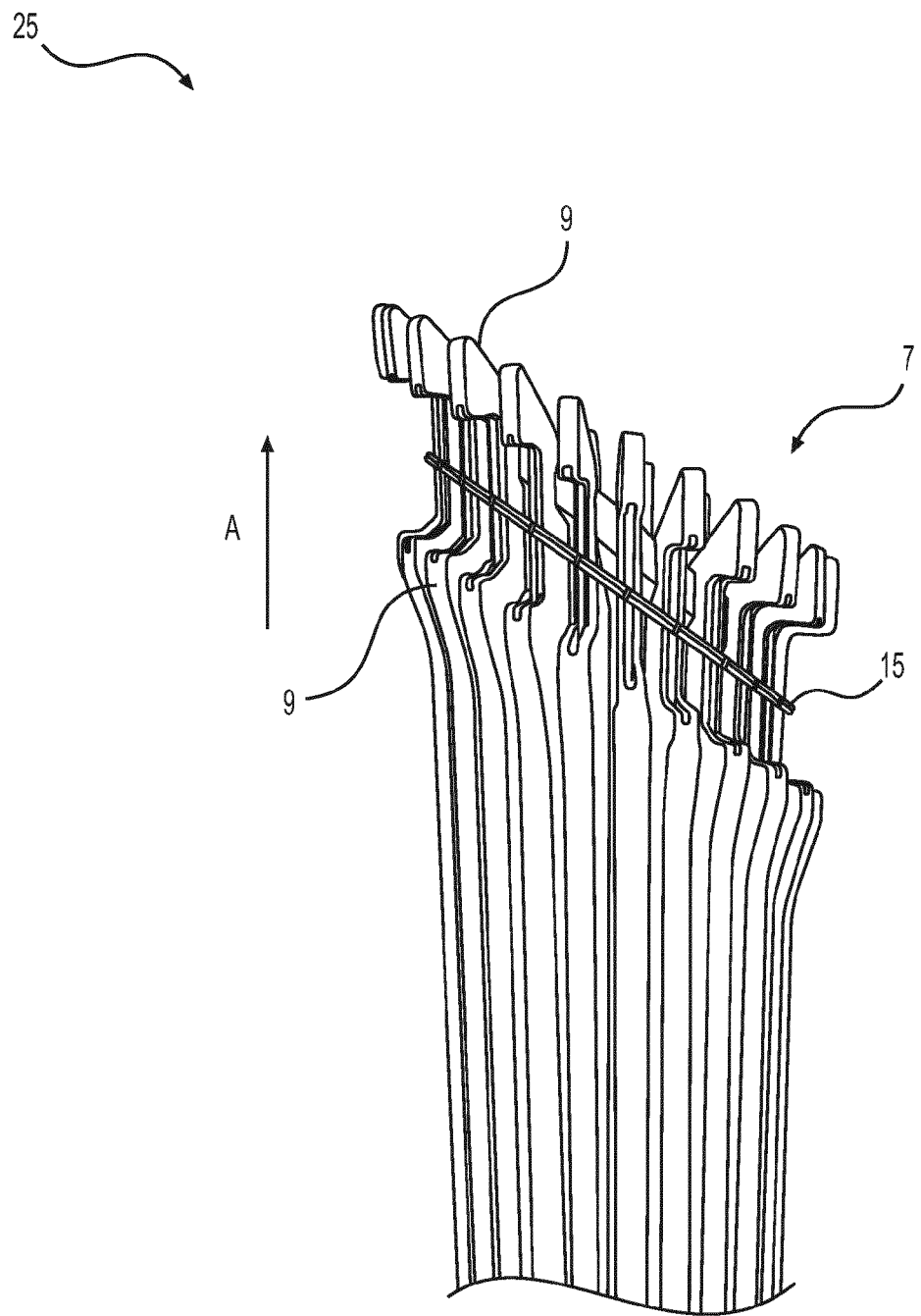
FIG. 11 is an expanded view of section X of the applicator shown in FIG. 3 seen from the opposite side as shown in FIG. 3 showing the applicator in the second expanded position.

FIG. 10 shows joining member 15 in a first unexpanded position located on seat 33 of actuation section 7 of applicator 30. FIG. 11 shows joining member 15 in a second, expanded position also located on seat 33 of actuation section 7 of applicator 30. As shown in FIG. 10, loops 16 may have a substantially circular, elliptical, or polygonal shape when joining member 15 is in the first, unexpanded position. In this first, unexpanded, position, the diameter of joining member 15 is smaller than the diameter of joining member 15 when in the second expanded position or the third joining position. Therefore, unexpanded joining member 15 is sufficiently small for insertion into the lumen of second hollow structure 8 as well as for insertion through a hole in the first hollow structure, e.g. the aorta. Joining member 15 is located on seat 33 and positioned proximate to a distal end of second hollow structure 8. During initial positioning, joining member 15 is in the unexpanded position and loops 16 still have the substantially circular, elliptical or polygonal shape as shown, for example, in FIGS. 7 and 10.

With joining member 15 positioned proximate to the distal end of the second hollow structure 8 on applicator 30, applicator 30 is employed to precisely position joining member 15 at the anastomosis site and joining member 15 is radially expanded to the second, expanded position shown in FIG. 11. Radial expansion is accomplished by straightening the curved portions of loops 16 by application of a tensile force thereon which results from the radial expansion of joining member 15 by applicator 30. As a result, the curved portions of loops 15 become straighter and the diameter of joining member 15 increases. The two substantially parallel structures that result from straightening the curved portions of loops 16 provide strength and radial stability for the expanded joining member 15 which results in no or only minimal recoil of joining member 15 after it is released from applicator 30.

When joining member 15 is in the second expanded position of FIG. 11, joining member 15 may be further actuated in a direction parallel to a longitudinal axis of a tubular member 2 of applicator 30. During this third actuation step, joining elements 18 (shown in FIGS. 8 and 9) are actuated for joining the first and second hollow structures by, for example, stapling. Joining elements 18 may be in the form of staples which are adapted for withstanding the tensile force exerted on joining member 15 when expanded, such that the staples or joining elements 18 do not get actuated (fired) prematurely.

In a preferred embodiment, joining member 15 has a substantially oval shape in its main plane. Joining member 15 is adapted to be seated on seat 33 located at the distal end of tubular member 2 of applicator 30, such that the main plane of joining member 15 is at about a 45° angle relative to the longitudinal axis of tubular member 2. Staple-like joining elements 18 attached at connection points 17 of joining member 15, are substantially evenly spaced around the circumference of joining member 15 such that the longitudinal axes of joining elements 18 are at about a 45° angle relative to the main plane of annular body 15 in the first, unexpanded position. Upon actuation, the applicator of the anastomosis system radially expands the substantially oval shape of joining member 15 to a larger oval shape whereby this angle changes from 45 to 60 degrees.

One advantage of joining member 15 according to the present invention is that by stretching the loops 16 sufficiently to become substantially straight, the resistance against recoil by plastic deformation of the loops 16 in the main plane of joining member 15 is substantially improved without increasing the thickness of loops 16. Minimizing the dimensions of the intraluminal material is advantageous in order to reduce the risk of intravascular thrombosis or chronic tissue proliferation. However, an adequate ability of joining member 15 to maintain its shape after expansion is required to minimize recoil of the expanded joining member 15 that may result from forces exerted on joining member 15 by the joined tissue. Due to the structure provided by straightening loops 16, the expanded joining member 15 offers significantly better resistance to elastic tissue forces exerted by the surrounding vessel walls than a similar joining member 15 having interconnecting loops 16 with a substantial residual curve remaining in the joining position.

This is advantageous since the tissue forces acting on joining member 15 may be considerable. For example, the hole in the sidewall of the aorta for making end-to-side anastomosis is preferably created by making a linear incision. As a result, joining member 15 needs to permanently deform this incision to a substantially circular or oval shape. By using a sufficiently strong joining member 15, a wider anastomosis orifice can be maintained by joining member 15, thereby offering superior flow properties between the first and second hollow structures. Additionally, an important practical advantage of a wide anastomosis orifice is that the aorta will not impede withdrawal of the applicator out of the anastomosis, thereby reducing the risk of the device being trapped inside the first hollow structure due to recoil of joining member 15 under pressure exerted by the wall of the first hollow structure.

Another advantage results from minimizing the amount of material that forms loops 16, namely, the force required to radially expand joining member 14 is reduced, thereby facilitating two-step actuation of the device using the preferred embodiment of applicator 30 described above. The joining elements 18 have to be able to withstand the longitudinal component of the force induced by radially expanding the joining member 15 to avoid premature actuation or firing of joining elements 18. The reduction in the force required to radially expand joining member 15 provided by use of loops 16 allows a corresponding reduction in the amount of material required for fabrication of sufficiently resilient joining elements 18 and, therefore, offers an improved joining member 15 for this additional reason.

A further advantage of minimizing the transverse thickness of interconnecting loops 16 is that plastic deformation of loops 16 to a substantially straight line is possible without tearing the material. This is desirable since substantial deformation of the interconnecting loops 16 is required to provide the desired amount of expansion of joining member 15. For example, it is typically desirable to achieve a 50 to 100 percent increase in the diameter of joining member 15 along both axes of the main plane.

One way to further increase the stability of joining member 15 is to increase the number of loops 16 between adjacent joining elements 18. Loops 16 of the annular body 15 may be interconnected by means of connecting elements 17. Connecting elements 17 provide locations for connecting joining elements 18 to joining member 15. The dimension of the connecting elements 17 in a plane perpendicular to the main plane of the joining member 15 is preferably substantially smaller than the largest distance between interconnecting loops 16 in this plane. One advantage of such connecting elements 17 is that during expansion, the rotational forces, exerted by joining member 15 on joining elements 18 relative to the main plane of joining member 15, are reduced, thereby simplifying the subsequent step of precise axial actuation of joining elements 18. Another advantage of connecting elements 17 is that the connection area to joining elements 18 is reduced, thus offering an increased length of joining elements 18 free for tissue engagement.

Some exemplary dimensions of the various components may be, for example, as follows. The joining elements may have a length of about 7.6 mm, a width of about 0.3 mm, and a taper from 0.4 mm to 0.2 mm. The connecting portions may be 0.3 mm square and have a loop width of 0.1 mm, and a height of 0.3 mm. The distance across each loop may be about 1 mm in the unexpanded state and about 2 mm in the expanded state.

One preferred embodiment of joining member 15 employs double connecting loops 16, connected by connecting elements 17, such that the connecting loops 16 apparently form O-shaped elements. In this embodiment, joining member 15 is oval-shaped, the shape being equivalent to an oblique section of a cylinder taken at the desired angle, in this case 45°. The main plane of the O-shape loops 15 is substantially the same as the main plane of joining member 15. Connecting elements 17, to which joining elements 18 are attached, are evenly spaced around the circumference of joining member 15.

The individual O-shaped loops 16 between adjacent joining elements 18 are each optimized for the intended deformation during radial expansion of joining member 15. Also, applicator 30 is provided with a main plane of a seat for holding joining member 15 that tilts from an initial 45° angle to a 60° angle relative to the longitudinal axis of tubular member 2 of applicator 30 during radial expansion. As a result, each 0-shaped loop 16 is a different shape when compared to adjacent O-shaped loops 16. Thus, joining member 15 is point symmetric in two lines oriented perpendicular to each other and located in the main plane, thereby defining four substantially identical sequences of varying O-shaped loops 16. The advantage of this embodiment is that the shape of joining member 15 may be optimized for a large variety of shapes before and after expansion of joining member 15 by use of differently shaped loops 16 and different lengths and sequences of shapes of loops 16.

It is also advantageous that joining elements 18 be in the form of staple-like elements, having at least two free ends and being attached to joining member 15 at a location between the free ends of the staple-like elements. Also, it is advantageous that the staple-like elements be tapered from a greater thickness proximate to connecting elements 17 towards the free ends thereof. Joining elements 18 are adapted and positioned to be actuated in a direction substantially parallel to a central axis of tubular member 2 of applicator 30, irrespective of the angle of joining member 15 relative to the longitudinal axis of applicator 30.

Joining elements 18 are designed to permanently join the walls of the first and second hollow structures, in order to create a secure and fluid-tight anastomosis. Since tissue trauma during device actuation is to be avoided, transmission of any component of the actuation force to the vessel walls should be minimized. To achieve this, a preferred embodiment of the applicator includes a seat for holding joining member 15, which seat 33 is formed by the outer and inner tubes of applicator 30 that comprise low profile, semi-circular anvils 9. These anvils 9 plastically deform joining elements 18 from an initial, substantially straight configuration into C-shapes or, preferably, O-shapes in such a way that during actuation, joining elements 18 are expelled from the anvils 9 of applicator 30 and engage the vessel walls in a manner similar to the manner of engagement of the curved needles used in hand suturing. Thus, during axial actuation to the joining position, joining elements 18 progressively protrude out of the anvils 9 and penetrate the vessel walls until eventually a substantially full circle has been formed by each joining element 18, thereby securely enclosing the tissue of both of the first and second hollow structures. The initial shape of joining elements 18 may be slightly curved in order to bias the plastic deformation in a desired direction and to facilitate holding separate joining elements 18 when employed, within their intended locations on seat 33 of tubular element 2.

Joining elements 18 may be provided in a large variety of shapes and may be integrally formed with joining member 15, or alternatively, may be constructed as separate elements that are subsequently connected to each other. The construction of joining elements 18 as separate parts may be advantageous for the construction of joining members 15 having complex geometries, or in order to take advantage of different material properties at different locations in joining member 15.

In one embodiment, for example, each joining element 18 may have at least two surfaces that are biased to move toward each other in order to clamp the walls of the hollow structures together, for example by using hyperelastic or memory materials like Nitinol. In this case, the walls of the hollow structures may be clamped together without substantial tissue penetration. To avoid excessive tissue compression, the surface area of joining elements 18 touching the walls of the hollow structures may be enlarged for the purpose of distributing the clamping force over a larger surface area.

It is common practice that a surgeon, prior to or during surgery, cuts the distal end of second hollow structure 8 which may be a prosthetic or natural vascular graft, to a length that fits the anatomy and a shape of a first hollow structure such as the aorta at the desired take-off angle. The shape of the end of the vascular graft is generally observed and cut by the surgeon, typically in a straight line after flattening and stretching the graft material in order to facilitate cutting with scissors. This practice often leads to imperfections including leakage of the anastomosis requiring subsequent repair, distortions of the geometry of the anastomosis and an imperfect angle of the axes of the first and second hollow structures relative to each other. All of these imperfections may contribute to unfavorable surgical outcomes including perivascular hematomas, anastomosis pressure gradients, intraluminal thrombus formation, thrombus embolization and even complete blood vessel or graft failure or obstruction.

Referring now to FIG. 12A, the present invention also relates to a cutting template 19 for precisely cutting the graft material of second hollow structure 8 into a desired shape for creating an anastomosis with another hollow structure having a desired take-off angle. Cutting template 19 is designed for use while holding the graft material in a flattened, stretched position. Template 19 includes an end that has a shape substantially corresponding to a sinusoidal shape. The sinusoidal shape may include variations to comply with requirements imposed by the specific behavior of the particular graft material that has been selected. The sides of template 19 may be provided with ridges on the edges thereof to facilitate proper alignment of template 19 with the longitudinal axis of the graft material. Template 19 may be used directly in combination with a sharp knife to cut the graft material by closely following the contour of template 19, or indirectly by, for example, tracing the outline of template 19 onto the graft material using a marker pen and then cutting with a pair of scissors.

The shape of the cutting template 19 is such that a heel 20 and toe 21 of the distal end of graft material have enough tissue/fabric for forming a reliable and leak-proof joint between the hollow structures. The graft is cut in a condition in which it is adapted to be connected to the aorta at an angle of approximately 60°. It is noted that when cutting the graft material 8, the graft material 8 is flattened, and in case of a harmonica shape, stretched.

An advantage of cutting the distal end of the graft material in this particular sinusoidal shape is that it minimizes miscapture of joining elements 18 proximate to toe 21 of the graft material and excessive tissue compression towards heel 20 of the graft material is prevented.

Figure 12B:
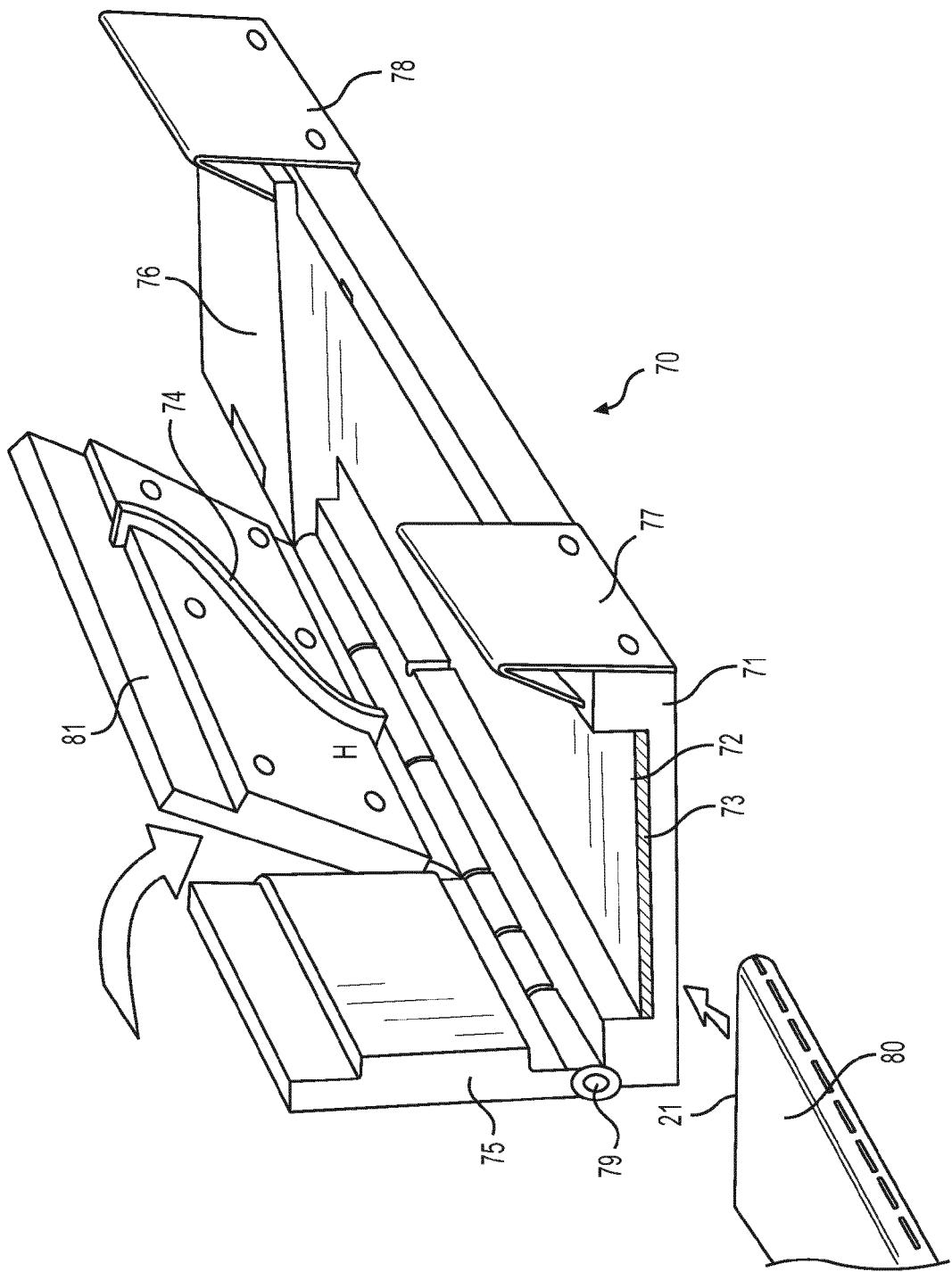
FIG. 12B shows a cutting device in accordance with an embodiment of the invention.

The present invention also relates to a cutting device 70 for precisely cutting the graft material, prosthetic or natural, of a vascular graft into a desired shape for creating an anastomosis with another hollow structure, an example of which is shown in FIG. 12B. The cutting device includes a housing 71 with at least one opening 72 for inserting the vascular graft into the housing 71 and configured for positioning a first end of the graft material for cutting. The cutting device also includes a support 73, such as a cutting mat, located inside the housing 71 and being adapted for supporting the vascular graft 80 during cutting thereof, and a cutting element 74, such as a knife blade, operatively associated with the support 72 for cutting the graft material 80 when supported on the support 72. The cutting element 74 is adapted to cut off at least a portion of one end of the graft material 80 to provide a cut graft material having a predetermined shape suitable for creating an anastomosis.

As shown in FIG. 12B, the cutting device 70 may also include a first clamping lid 75 and a second clamping lid 76 for clamping the graft material 80 during cutting. First and second clamping lids 75, 76 are attached to housing 71 by a hinge 79. Lock/release mechanisms 77, 78 may be used to lock and release the first and second clamping lids 75, 76, respectively. Cutting device 70 also includes a cutting lid 81 to which the cutting mechanism 74 is affixed.

For cutting, the graft material 80 is first folded along marker line 82. All of the first and second clamping lids 75, 76 and the cutting lid 81 are opened and the graft material is positioned inside the channel formed by housing 71 atop the cutting mat 72. The first and second clamping lids 75, 76 are then closed and locked by the lock/release mechanisms 77, 78 to firmly hold the graft material 80 in place for cutting. Cutting lid 81 is then closed to cut the graft material 80 to the desired shape. Upon completion of cutting, the toe 21 of the graft material will be positioned at location T and the heel 20 of the graft material 80 will be positioned at location H. Once cutting is complete, the lock/release mechanisms 77, 78 are released, and each of the first and second clamping lids 75, 76 and the cutting lid 81 are opened for removal of the cut graft material 80 from the cutting device 70.

The invention further relates to a method of cutting a vascular graft for use during anastomosis construction using a cutting device for cutting the graft material. The method includes steps of: inserting at least one end of the vascular graft into a housing of the device, positioning the vascular graft on a support of the device inside the housing, and cutting at least one end of the vascular graft into a desired shape.

An advantage of the cutting template and device according to the present invention is that by reliably cutting the vascular graft material into the desired shape, the reliability and repeatability of the anastomosis is substantially improved, either in case of hand suturing or when created using a mechanical anastomosis device. For a mechanical device, controlling the amount of vascular graft material that is captured by each joining element 18 within defined limits improves the quality of the anastomosis. The same type of cutting precision is not likely to be achieved by a surgeon manually cutting the vascular graft material along a linear cut, for example using a pair of scissors.

If the plane through the end of the vascular graft is cut at an angle different from 90° relative to its longitudinal axis, too much vascular graft wall material may be available in some areas such as heel 20 of this vascular graft relative to other areas. As a result, too much vascular graft wall material may end up being captured by joining elements 18 in some areas of the circumference of the anastomosis. Especially in case of a prosthetic vascular graft, the wall material is very difficult to compress. Consequently, reduced space will be left for the vessel wall of the first hollow structure, for example the aorta, within joining elements 18 after being actuated or closed. Thus, excessively high compressive forces on the tissue may result, potentially leading to instantaneous tissue rupture and leaking or other dangerous situations like necrosis of the aorta or late aneurysm formation. Alternatively, joining elements 18 may fail to capture areas of the vascular graft where insufficient material is available and, consequently, no connection is formed in these areas, resulting in leakage.

By cutting the end of the vascular graft material into a predefined shape that has been optimized for the specific graft material properties and the geometry of the anastomosis, the cut end will closely fit the opening in the outer surface of the wall of the first hollow structure. Especially in combination with the support member described above, the desirable amount of wall material at the end of the vascular graft will be presented to joining elements 18, which, together with the correct orientation of the distal edge of the graft material, substantially improves the reliability and reproducibility of the outcome.

The invention relates to a tubular graft material having at least one end thereof that is shaped such that, when the graft is flattened, the edge of the end substantially corresponds to a sinusoidal shape. The advantage of cutting the distal edge in a sinusoidal shape while the graft material is in a flattened position is that after the vascular graft is returned to a tubular shape, the resultant distal edge will very closely fit to the outer surface of the wall of the first hollow vessel for the construction of an end-to-side anastomosis at a take-off angle less than 90°.

It is often desirable to carry out surgical repair of organs and other structures using minimally or less invasive strategies like port-access procedures and approaches through blood vessels. Especially when working on vital organs, like the heart and aorta, novel technologies are required in order to realize safe and reliable results, improve outcomes and avoid the necessity of using the heart lung machine. Examples of such novel technologies are trans-femoral and trans-apical replacements of the aortic valve. In these procedures, access to the arterial system and heart is acquired through a femoral artery, or, in case of the trans-apical approach, directly through the apex of the left main chamber of the heart using a small intercostal incision. A folded valve deployed using a delivery device is then positioned exactly at the desired spot using advanced imaging technologies like, for example, a CT scan, MRI and TEE (trans-oesophageal ultrasound). The valve is then deployed, in most cases by expanding the device in some particular way. After withdrawing the delivery device and closing the access site, this minimally invasive heart valve replacement procedure leaves the patient without a large wound and obviates the need for a cardiopulmonary bypass using a heart lung machine. The advantages are numerous, the outcomes are significantly improved and these procedures allow weaker patients to be treated and can considerably speed up recovery.

Novel devices for trans-vascular repair or replacement of the mitral valve are under development as well. Mitral valve regurgitation is a common cause of heart failure, often in combination with or even due to a reduced pump capacity of the left main chamber of the heart due to, for example, myocardial infarction. Treatment of this valve malfunction may significantly improve quality of life and even life expectancy. The often reduced pump capacity of the heart increases the risks of conventional surgery. Novel devices for trans-vascular treatment potentially offer attractive alternatives for such patients. The delivery of such devices, however, needs special attention. One way to reach the mitral valve is to pass a guide wire through the femoral vein into the right atrium of the heart and then to puncture the atrial septum in order to reach the left atrium and mitral valve. This approach is complicated due to the need to make a hole in the atrial septum, that later needs to be closed, and due to the relatively sharp bends in the trajectory that must be negotiated by the guide wire. Another way to reach the mitral valve position involves puncturing the apex of the left ventricle of the heart through a small thoracotomy, very similar to the method used for trans-apical delivery of an aortic valve mentioned above. This approach has the advantage of being very straightforward, but the disadvantage of necessitating the sacrifice of some myocardium when closing the hole in the apex of the heart. Since the heart often has a reduced pump capacity in typical patients, loss of myocardial tissue should be avoided or at least minimized There is a need for a straightforward way to provide access to the beating heart, allowing large caliber devices to be deployed at a desired location inside the heart.

One solution to this problem involves connecting one end of a prosthetic tube to the left atrium of the heart using an anastomosis. If the prosthetic tube is sufficiently long that the other end can remain outside the thorax it can be used to facilitate closed chest procedures. In order to create such an anastomosis on a beating heart in a minimally invasive way, the anastomosis is preferably constructed using a one-shot anastomotic device, for example, an anastomotic device as described above. The anastomotic device can be delivered to the anastomosis site over a guide wire and can be equipped with a tapered nose-cone to facilitate atrial wall penetration. The nose-cone can have cutting edges or a built-in knife as described, for example, in WO2005/086841 in relation to FIG. 66A. An example of a suitable method and procedure is described below.

Figure 13A:
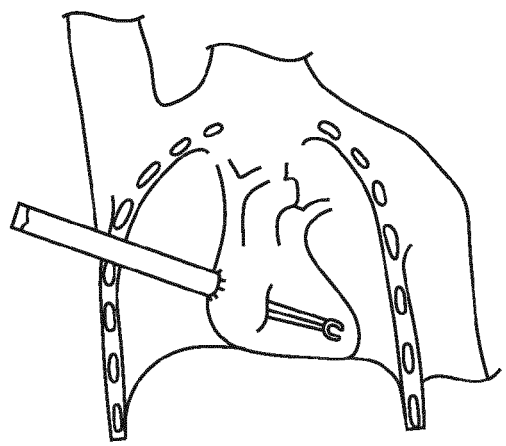
FIGS. 13A-13D show a schematic representation of a method for providing access to the left atrium of the heart.
Figure 13B:
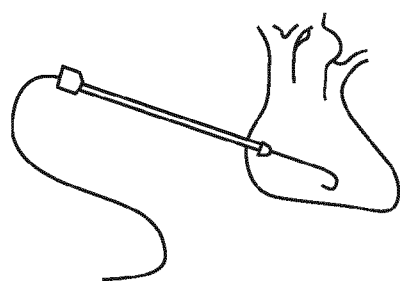
Figure 13C:
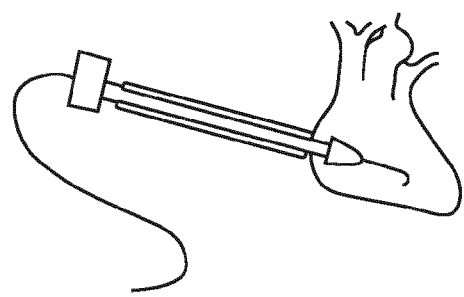

Referring to FIGS. 13A-13D, after deflation of the right lung, the pericardium is opened using standard, port-access video-assisted techniques. Through a small intercostal incision, a long needle is inserted into the thoracic cavity. Subsequently, the left atrium of the heart is punctured at a desired spot, for example, the free wall in the area between the pulmonary veins as shown in FIG. 13A. A guide wire is then inserted through the needle into the left atrium as shown in FIG. 13B. The needle is removed and then an anastomotic device as described above, loaded with a prosthetic graft of the desired diameter, for example 10 mm, is then passed over the guide wire into the thoracic cavity and is advanced towards the left atrium. By pushing the anastomotic device against the atrial wall, the nose-cone penetrates the wall and the anastomotic device is further advanced and positioned for creating the anastomosis as shown in FIG. 13C.

Figure 13D:
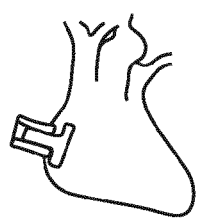

After deploying the device, the prosthetic graft is hemostatically connected to the left atrium and the anastomotic device can be removed. The prosthetic graft is then clamped outside the thoracic cavity. Alternatively, a valved stop can be used to close the prosthetic graft while allowing easy access for devices into the prosthetic graft as shown in FIG. 13D. The same guide wire can then be repositioned at the desired location inside the heart using, for example, ultrasound imaging. Then the device for carrying out the intracardiac repair procedure, for example, a valve replacement device, is advanced through the prosthetic graft into the correct position. After the valve has been delivered and the guide wire(s) have been removed, the prosthetic graft can be closed near the heart, for example, by using one or more large hemoclips. The prosthetic graft can then be cut near to these clips and the excess graft material can be removed. Alternatively, a closure device such as an obdurator such as a silicon stop having a ridge, may be deployed. The closure device can be inserted in a compressed state and then be deployed by allowing it to expand at the desired location with the ridge being positioned inside the left atrial cavity to avoid the device being pushed out by the blood pressure. In order to optimize safety, a balloon device can be kept ready as a bailout device. In case of bleeding, for example due to inadvertently tearing the anastomosis, the balloon can be inserted into the left atrium over the guide wire and can be inflated. By pulling the inflated balloon backwards into the anastomosis, bleeding can be controlled allowing time for repair measures.

There are several advantages of the method described above. The diameter of the prosthetic graft can be very wide, allowing less tightly compressed devices, which may improve the durability of biological valves deployed in this manner. Also, this method can provide a line of access that is substantially parallel to the longitudinal axis of the left ventricle, which is ideal for positioning and delivery of a mitral valve prosthesis. Further, this method can be used on the closed, beating heart in a minimally invasive way. Lastly, no myocardial tissue needs to be sacrificed, thereby maintaining the integrity of the patient's left ventricle as much as possible.

This method can be used for other purposes as well. For example, tricuspid valve replacement can be carried out by connecting a prosthetic graft to the right atrium in a very similar way. Even aortic valve replacement may benefit from this method, for example, by enabling connection of a prosthetic graft to the ascending aorta through a small upper sternotomy or to any other part of the arterial system having an adequate diameter and being easy to reach through a small skin incision.

Unless stated otherwise, terms such as "first" and "second" are used to arbitrarily distinguish between the elements such terms describe. Thus, these terms are not necessarily intended to indicate temporal or other prioritization of such elements. Further, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles.

Although the invention is described herein with reference to specific embodiments, various modifications and changes can be made without departing from the scope of the present invention as set forth in the claims below. Accordingly, the specification and figures are to be regarded in an illustrative rather than a restrictive sense, and all such modifications are intended to be included within the scope of the present invention. Any benefits, advantages, or solutions to problems that are described herein with regard to specific embodiments are not intended to be construed as a critical, required, or essential feature or element of any or all the claims.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

In this specification including any claims, the term "each" may be used to refer to one or more specified characteristics of a plurality of previously recited elements or steps. When used with the open-ended term "comprising," the recitation of the term "each" does not exclude additional, unrecited elements or steps. Thus, it will be understood that an apparatus may have additional, unrecited elements and a method may have additional, unrecited steps, where the additional, unrecited elements or steps do not have the one or more specified characteristics.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

The embodiments covered by the claims in this application are limited to embodiments that (1) are enabled by this specification and (2) correspond to statutory subject matter. Non-enabled embodiments and embodiments that correspond to non-statutory subject matter are explicitly disclaimed even if they fall within the scope of the claims.

All documents mentioned herein are hereby incorporated by reference in their entirety or alternatively to provide the disclosure for which they were specifically relied upon.

The applicant(s) do not intend to dedicate any disclosed embodiments to the public, and to the extent any disclosed modifications or alterations may not literally fall within the scope of the claims, they are considered to be part hereof under the doctrine of equivalents.

What is claimed is:

1. An anastomosis device for creating an anastomosis between first and second hollow structures, comprising:
   an expandable joining member having:
   a) an oval or polygonal ring-shaped body which is configured to permit radial expansion of said body to expand said joining member from a first position to a second position having a second, larger diameter than the first position, and
   b) a plurality of joining elements for joining the hollow structures and which joining elements are connected to the body;
   a tubular member having a seat configured to receive the joining member, the tubular member being configured to position the joining member, when positioned on said seat, at least partially within the second hollow structure and proximate to a distal end of the second hollow structure;
   an actuator for actuating the joining member in a substantially radial direction relative to a longitudinal axis of the tubular member to expand the joining member when the joining member is positioned on said seat;
   an external axially movable, longitudinally splittable tubular support member that is configured to be split along a longitudinal line of weakness into parts that are removable from the joining member and is configured to provide radial support to the second hollow structure at the location proximate to the distal end of the second hollow structure during actuation of the joining member.

2. The anastomosis device according to claim 1, wherein the seat of the tubular member is configured for holding the joining member, such that a plane intersecting joining elements of said joining member is at an angle other than 90 degrees relative to the longitudinal axis of the tubular member and a distal end of the tubular support member forms a plane at an angle other than 90 degrees relative to the longitudinal axis of the tubular member.

3. The anastomosis device according to claim 1, wherein the actuator is configured for actuating the plurality of joining elements by expanding the joining elements from a first position having a first diameter of said joining elements to a second position having a second, diameter of said joining elements that is larger than said first diameter.

4. The anastomosis device according to claim 3, wherein the actuator is further configured for actuating the joining elements in a direction substantially parallel to the longitudinal axis of the tubular member in order to bring the joining elements into a second position in which the first and second hollow structures are joined.

5. The anastomosis device according to claim 1, wherein the tubular support member is provided with a connecting part for attaching the tubular support member to the tubular member, at a location proximate to a proximal end of the tubular member.

6. The anastomosis device according to claim 1, wherein the tubular support member comprises a tubular part that is configured to surround at least a part of the tubular member in a manner whereby at least a part of the second hollow structure is also surrounded by said tubular part when said second hollow structure is positioned on said anastomosis device and the tubular part is configured to separate along a substantially longitudinal direction in order to be removable from the tubular member.

7. The anastomosis device according to claim 1, wherein the tubular support member is configured for retaining the second hollow structure in association with the tubular member, and the tubular support member is further configured to release the second hollow structure from the tubular member after the first and second hollow structures have been joined.

8. The anastomosis device according to claim 7, wherein the tubular support member is configured to clamp at least a portion of the tubular member and at least a portion of the second hollow structure in order to retain the second hollow structure in association with the tubular member.

9. The anastomosis device according to claim 7, wherein a tubular part of the tubular support member comprises a ribbed section located on an inner surface of the tubular part of the tubular support member and said ribbed section is configured for engaging and positioning the second hollow structure.

10. The anastomosis device according to claim 1, wherein the tubular support member is provided with a resilient element configured to allow limited axial movement of a portion of the tubular support member with respect to the tubular member when said tubular support member is attached to said tubular member.

11. The anastomosis device according to claim 1, wherein the tubular support member has resilient properties to allow limited movement of the tubular support member relative to the tubular member.

12. The anastomosis device according to claim 1, wherein the tubular support member is movable between a viewing position, in which a user is able to see a distal end of the second hollow structure positioned on said anastomosis device in order to facilitate positioning the joining member, and an actuation position in which actuation position the joining member is actuated by the actuator for joining the first and second hollow structures.

13. The anastomosis device according to claim 1, wherein the tubular support member comprises an orientation element for orienting the second hollow structure relative to the support member.

14. The anastomosis device according to claim 1, further comprising a grip located proximate to a proximal end of the tubular member and wherein said grip is configured to facilitate gripping of the anastomosis device by a user and a mechanical, electrical, pneumatic or hydraulic controller configured for controlling the actuator, said controller being mounted on the grip of the anastomosis device.

15. A method of creating an anastomosis between first and second hollow structures using the anastomosis device of claim 1, the method comprising steps of:
   inserting the tubular member in the second hollow structure with the plurality of joining elements positioned on the seat
   positioning the plurality of joining elements proximate to a distal end of the second hollow structure,
   actuating the plurality of joining elements in a substantially radial direction relative to a longitudinal axis of the tubular member,
   providing radial support to the second hollow structure at least proximate to a distal end of the second hollow structure during actuation of the plurality of joining elements,
   retaining the second hollow structure in a position relative to at least the tubular member by means of the tubular support member,
   releasing the second hollow structure after the first and second hollow structures have been joined, and
   longitudinally splitting the tubular support member along a longitudinal line of weakness for removing the tubular support member from the tubular member and the second hollow structure, after the first and second hollow structures have been joined.

16. The method according to claim 15, wherein the step of actuating the plurality of joining elements comprises the step of moving said plurality of joining elements substantially radially relative to the longitudinal axis of the tubular member from the first position to a joining position wherein said joining elements are at a greater distance from each other in the joining position than in the first position and the step of actuating the plurality of joining elements comprises a step of actuating said plurality of joining elements in a direction parallel to the longitudinal axis of the tubular member for bringing the plurality of joining elements into a third position in which the first and second hollow structures are joined by said joining elements.

17. The method according to claim 15, further comprising a step of connecting the tubular support member to the tubular member.

* * * * *